United States Patent
Eidenschink et al.

(10) Patent No.: US 12,420,057 B2
(45) Date of Patent: *Sep. 23, 2025

(54) APPARATUS AND METHOD FOR SENSOR DEPLOYMENT AND FIXATION

(71) Applicant: Pacesetter, Inc., Sylmar, CA (US)

(72) Inventors: Tracee Eidenschink, Wayzata, MN (US); Jin Woo Park, Suwanee, GA (US); Jason A. White, Cocoa Beach, FL (US)

(73) Assignee: Pacesetter, Inc., Sylmar, CA (US)

( * ) Notice: Subject to any disclaimer, the term of this patent is extended or adjusted under 35 U.S.C. 154(b) by 254 days.

This patent is subject to a terminal disclaimer.

(21) Appl. No.: 18/310,731

(22) Filed: May 2, 2023

(65) Prior Publication Data
US 2023/0263992 A1 Aug. 24, 2023

Related U.S. Application Data

(63) Continuation of application No. 17/120,385, filed on Dec. 14, 2020, now Pat. No. 11,672,949, which is a
(Continued)

(51) Int. Cl.
*A61M 25/00* (2006.01)
*A61M 25/09* (2006.01)

(52) U.S. Cl.
CPC ........ *A61M 25/003* (2013.01); *A61M 25/005* (2013.01); *A61M 25/0097* (2013.01);
(Continued)

(58) Field of Classification Search
None
See application file for complete search history.

(56) References Cited

U.S. PATENT DOCUMENTS

| | | |
|---|---|---|
| 6,855,115 B2 | 2/2005 | Fonseca et al. |
| 7,147,604 B1 | 12/2006 | Allen |

(Continued)

FOREIGN PATENT DOCUMENTS

| | | |
|---|---|---|
| CN | 103635160 A | 3/2014 |
| CN | 105764411 A | 7/2016 |

OTHER PUBLICATIONS

International Search Report and Written Opinion for corresponding PCT Application No. PCT/US2019/056060 dated Jun. 25, 2020 (15 pages).
(Continued)

*Primary Examiner* — Manuel A Mendez
(74) *Attorney, Agent, or Firm* — Dean D. Small; The Small Patent Law Group, LLC.

(57) ABSTRACT

A delivery system for an intracorporeal device includes a sheath defining one or more lumens shaped to receive a delivery catheter or shaft and a guidewire. The system may include a delivery shaft having a distal coupling feature adapted to releasably couple with a proximal coupling feature of the intracorporeal device. The delivery system may further include a hub through which the delivery shaft and guidewire are passed. The delivery shaft may be coupled to a feature, such as a knob, that enables manipulation of the delivery shaft to decouple the distal fixation feature from the proximal fixation feature of the intracorporeal device in order to deploy the intracorporeal device within a patient.

24 Claims, 15 Drawing Sheets

Related U.S. Application Data continuation of application No. 16/162,147, filed on Oct. 16, 2018, now Pat. No. 10,894,144.

(52) U.S. Cl.
CPC . *A61M 25/0905* (2013.01); *A61M 2025/0031* (2013.01); *A61M 2025/0034* (2013.01)

(56) References Cited

U.S. PATENT DOCUMENTS

| | | | |
|---|---|---|---|
| 7,481,771 B2 | 1/2009 | Fonseca et al. | |
| 7,574,792 B2 | 8/2009 | O'Brien et al. | |
| 7,699,059 B2 | 4/2010 | Fonseca et al. | |
| 8,353,841 B2 | 1/2013 | White et al. | |
| 9,265,428 B2 | 2/2016 | O'Brien et al. | |
| 10,894,144 B2 | 1/2021 | Eidenschink | |
| 11,672,949 B2 * | 6/2023 | Eidenschink | A61B 5/6876 604/93.01 |
| 2004/0133220 A1 | 7/2004 | Lashinski et al. | |
| 2004/0153146 A1 | 8/2004 | Lashinski et al. | |
| 2008/0071339 A1 | 3/2008 | Stalker et al. | |
| 2010/0174233 A1 | 7/2010 | Kuban et al. | |
| 2015/0201885 A1 | 7/2015 | White et al. | |
| 2018/0289487 A1 | 10/2018 | Alexander et al. | |

OTHER PUBLICATIONS

International Preliminary Report on Patentability PCT Application No. PCT/US2019/056060 dated Apr. 29, 2021 (10 pages).
Office Action for corresponding CN Application No. 201980060549.0 dated Sep. 21, 2023 (24 pages).

* cited by examiner

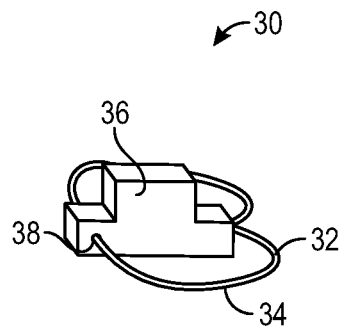
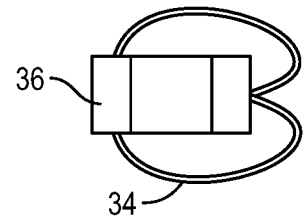
FIG. 1  FIG. 2
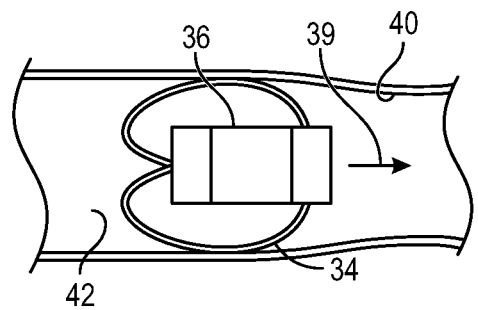
FIG. 3
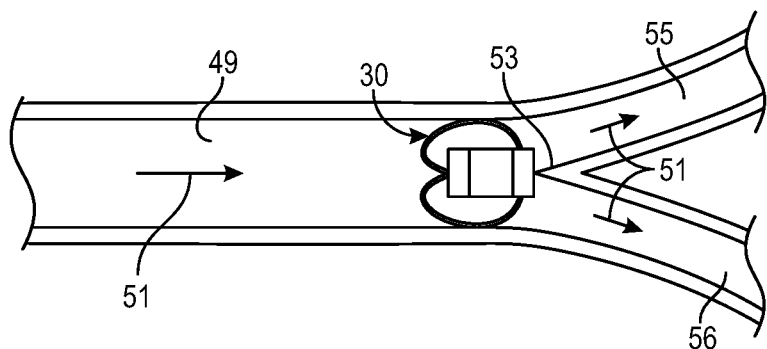
FIG. 4

APPARATUS AND METHOD FOR SENSOR DEPLOYMENT AND FIXATION

REFERENCE TO RELATED APPLICATIONS

The present application is a continuation of Ser. No. 17/120,385, titled "APPARATUS AND METHOD FOR SENSOR DEPLOYMENT AND FIXATION" which was filed on 14 Dec. 2020, which is a continuation application of, and claims priority to, U.S. application Ser. No. 16/162,147, Titled "APPARATUS AND METHOD FOR SENSOR DEPLOYMENT AND FIXATION" which was filed on 16 Oct. 2018 (now U.S. Pat. No. 10,894,144, issued 19 Jan. 2021, the complete subject matter of which is expressly incorporated herein by reference in its entirety.

TECHNICAL FIELD

This disclosure relates generally to implantation of intracorporeal devices into vessels and to systems and methods of delivering such intracorporeal devices to predetermined locations within the vessel.

BACKGROUND

In recent years, the long-sought goal of implantable biosensors has begun to see realization and, in some cases, clinical use. As this concept has seen continued research and development, issues regarding intracorporeal fixation of the sensor have come to light. Particularly within blood vessels, the sensor is subjected to a continuous, pulsatile flow. This is a difficult environment in which to secure a sensor or other apparatus reliably without unduly restricting blood flow or impairing the vessel wall. One major vessel of interest in the realm of cardiology is the pulmonary artery. The pulmonary artery is a particularly challenging location in which to secure an intracorporeal device because, in addition to the above considerations, the vessel is especially thin, compliant and prone to perforation.

Design considerations for an ideal fixation device intended for intravascular fixation are outlined as follows. The fixation device should be passive and maintain a separation distance between the sensor and the vessel wall to maintain blood flow past the sensor. The deployed size and radial strength of the device should be sufficient to prevent its migration into vessels that would be occluded by the dimensions of the sensor while creating minimal stress concentrations where the fixation device contacts the vessel wall. Alternatively, intracorporeal devices can be designed sufficiently small in size so that when deployed in organs or regions with sufficiently redundant blood flow, the device can embolize on its own without harming the organ or the host. Finally, the fixation device should be sufficiently versatile as not to depend, within physiologically relevant ranges, on the size of the vessel in order to maintain its position.

Thus, a need exists for devices and methods for fixing intracorporeal devices and, in particular, for delivery and fixation of such devices in a safe, simple and predictable manner.

SUMMARY

In one aspect of the present disclosure, an intracorporeal device delivery system is provided. The delivery system includes a delivery shaft including a distal coupling feature and a sheath adapted to receive a guidewire and defining a delivery shaft lumen, the delivery shaft being disposed within the delivery shaft lumen. The delivery system further includes an intracorporeal device having a proximal coupling feature and a device body, the device body defining an axial envelope extending proximally from the device body. The distal coupling feature is releasably coupled to the proximal coupling feature such that, when coupled, the distal coupling feature is disposed within the axial envelope defined by the device body.

In certain implementations, the sheath defines a guidewire lumen separate from the delivery shaft lumen and shaped to receive the guidewire.

In another implementation, the distal coupling feature of the delivery shaft is a threaded extension extending distally from the delivery shaft and the proximal coupling feature of the intracorporeal device is a threaded hole shaped to receive the distal coupling feature.

In yet another implementation, the intracorporeal device delivery system further includes a hub coupled to a proximal end of the delivery shaft. The hub may include a shaft manipulation feature coupled to the delivery shaft and configured to release the distal coupling feature from the proximal coupling feature when manipulated. In one example implementation, the shaft manipulation feature is a rotatable knob coupled to the delivery shaft such that rotation of the rotatable knob rotates the delivery shaft to decouple the distal coupling feature from the proximal coupling feature.

In certain implementations, the hub includes at least one port in communication with an auxiliary lumen of the sheath such that the port is in fluid communication with a distal end of the sheath. The auxiliary lumen may, in some implementations, be one of the distal shaft lumen or the guidewire lumen.

The sheath may, in certain implementations, include braided tubing, such as Pebax tubing.

In certain implementations, the intracorporeal device includes a guide defining a passage shaped to receive the guidewire, the passage disposed outside the axial envelope.

In another aspect of the present disclosure, an intracorporeal device delivery system is provided. The delivery system includes a delivery shaft including a distal coupling feature extending from a distal end of the delivery shaft and including a threaded extension. The delivery system further includes a sheath adapted to receive a guidewire and defining a delivery shaft lumen, the delivery shaft being disposed within the delivery shaft lumen. The delivery system also includes an intracorporeal device having a proximal coupling feature and a device body, the device body defining an axial envelope extending proximally from the device body and the proximal coupling feature including a threaded hole shaped to receive the threaded extension of the delivery shaft. The distal coupling feature is releasably coupled to the proximal coupling feature such that, when coupled, the distal coupling feature is disposed within the axial envelope defined by the device body.

In certain implementations, the sheath defines a guidewire lumen separate from the delivery shaft lumen and shaped to receive the guidewire.

In another implementation, the distal coupling feature of the delivery shaft is a threaded extension extending distally from the delivery shaft and the proximal coupling feature of the intracorporeal device is a threaded hole shaped to receive the distal coupling feature.

In yet another implementation, the intracorporeal device delivery system further includes a hub coupled to a proximal end of the delivery shaft. The hub may include a rotatable knob coupled to the delivery shaft such that rotation of the rotatable knob rotates the delivery shaft to decouple the distal coupling feature from the proximal coupling feature. In certain implementations, the rotatable knob may be coupled to the delivery shaft by a set screw extending through the rotatable knob.

In certain implementations, the hub includes at least one port in communication with an auxiliary lumen of the sheath such that the port is in fluid communication with a distal end of the sheath. The auxiliary lumen may, in some implementations, be one of the distal shaft lumen or the guidewire lumen.

The sheath may, in certain implementations, include braided tubing, such as Pebax tubing.

In certain implementations, the intracorporeal device includes a guide defining a passage shaped to receive the guidewire, the passage disposed outside the axial envelope.

In yet another aspect of the present disclosure, an intracorporeal device delivery system is provided. The delivery system includes a sheath defining each of a delivery catheter lumen and a guidewire lumen separate from the delivery catheter lumen and a delivery catheter extending through at least a portion of the delivery catheter lumen. The system further includes an intracorporeal device releasably coupled to a distal portion of the delivery catheter and a hub coupled to a proximal end of the sheath, the hub including a port. A cross-sectional area of the delivery catheter lumen exceeds a cross-sectional area of the delivery catheter such that an annular volume is defined between the delivery catheter and an inner wall of the delivery catheter defining the delivery catheter lumen, the annular volume being in communication with the port.

Other objects, features, and advantages of the present disclosure will become apparent upon reading the following specification, when taken in conjunction with the drawings and the appended claims.

BRIEF DESCRIPTION OF THE DRAWINGS

In order to describe the manner in which the above-recited and other advantages and features of aspects of this disclosure can be obtained, a more particular description of the implementations briefly described above will be rendered by reference to specific embodiments thereof which are illustrated in the appended drawings. It should be noted that the figures are not drawn to scale, and that elements of similar structure or function are generally represented by like reference numerals for illustrative purposes throughout the figures. These drawings depict only example implementations of the present disclosure and are not therefore to be considered to be limiting of its scope. Implementations of the disclosure will be described and explained with additional specificity and detail through the use of the accompanying drawings.

FIG. 1 is an isometric view of a first embodiment of an implant assembly according to the present disclosure, the implant assembly having two opposed wire loops.

FIG. 2 is a top view of the implant assembly of FIG. 1.

FIG. 3 is a cutaway view of a vessel showing the implant assembly of FIG. 1 fixed therein.

FIG. 4 is a cutaway view of a pulmonary arterial vessel showing the implant assembly of FIG. 1 fixed therein.

DETAILED DESCRIPTION

Figure 5:
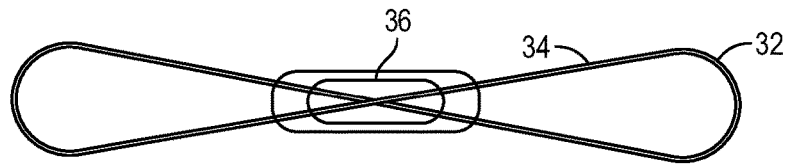
FIG. 5 is a top view of a second embodiment of an implant assembly according to the present disclosure, the implant assembly having opposed wire loops.

An implant assembly as described in this disclosure generally includes an intracorporeal device and an anchoring structure used to stabilize the intracorporeal device in the body, such as in a vessel. Delivery systems which deploy and secure the implant assembly in a desired location in a vessel are also provided and generally include a delivery apparatus and the implant assembly to be delivered. In certain implementations, the intracorporeal device may be a pressure sensor, further described below. The anchoring structure may be a structure capable of being introduced into the body via a delivery apparatus, such as a catheter, and then lodged within the vessel. Anchoring structures of this disclosure may include structure including opposed wire loops, radial wire array structures, and daisy petal structures, all further described below.

All of the implant assemblies of this disclosure obstruct approximately 50% or less of the cross-sectional area of the vessel in which they are disposed. The implant assemblies may, in certain implementations, obstruct 20% or less of the cross-sectional area of the vessel. Minimizing the obstruction of flow within the vessel allows the intracorporeal device to remain secured in position in a vessel without creating significant impact to the flow within the vessel. Furthermore, the implant assemblies disclosed herein generally rely on the physical size of the expanded anchoring structure coupled with the stiffness of the wire used to construct the anchoring structure to prevent further distal movement. This is contrary to stent or vena cava filter type mechanisms wherein fixation is achieved by radially exerted force and/or hook or barb attachment features.

Anchoring structures of this disclosure may be formed from metal or polymer and may be in the form of a wire structure. The wire diameter of the anchoring structures of the current disclosure lies in the range of about 0.001 to about 0.015 inches. The material comprising the wire can be any biocompatible material known in the art that possess sufficient elastic properties to be useful for the purpose at hand. In one implementation the material comprising the wire is a polymer. In an alternative implementation the material comprising the wire may be a metal, such as nitinol, stainless steel, eligiloy, cobalt chrome alloys, or any other suitable metal. In a further implementation, if the wire is comprised of a metal material, the biocompatible wire is coated with a dielectric material, such as, but not limited to, PTFE, polyurethane, parylene and diamond-like carbon (DLC) so as not to pose electromagnetic interference with the function of the intracorporeal device when the device comprises an RF sensor. The term "wire" used throughout this document should be construed, without limitation, to embody the entire contents of this paragraph.

The phrase "intracorporeal device" as used in this document includes any, and all, implantable devices. Such devices can include, e.g., sensors that measure chemical and/or physical parameters, devices configured to perform a function, e.g. drug delivery devices, and combinations of the same. The intracorporeal device may communicate with external electronics either wirelessly or by being placed in physical contact with said electronics, such as by a wire.

The exemplary device disclosed herein describes a coating as a feature. It should be understood that this disclosure encompasses an intracorporeal device constructed of a polymeric material and that the same construction techniques used to create the anchoring structures could be employed by threading the wires directly through the polymeric material of the device. Additionally, materials used in the construction of such intracorporeal devices, coatings or otherwise, could be any biocompatible polymer. Such materials include but are not limited to biocompatible silicone rubber, FEP, PTFE, urethane, PVC, nylon, and polyethylene.

The intracorporeal device used to couple to the anchoring structures described below has a width of about 0.5 to about 4 mm, a height of about 0.5 to about 4 mm, and a length of about 0.5 to about 12 mm. In one implementation, the intracorporeal device has a width of approximately 3.2 mm, a height of approximately 2 mm, and a length of approximately 10 mm. Examples of such devices are disclosed in commonly owned U.S. Pat. Nos. 6,855,115; 7,147,604; 7,481,771; 7,574,792; 7,699,059; and 9,265,428, each of which are incorporated herein by reference.

A. Wire Loop Structures

One example implant assembly adapted for deployment and fixation within a vessel includes an intracorporeal device and a wire structure having wire loops. The loops may traverse the length of the device or may be limited to one end of the device. As shown in FIGS. 1 and 2, one implementation of an implant assembly 30 having a double loop structure 32 includes a wire 34 attached to an intracorporeal device 36 at an attachment site (not shown). The wire 34 is threaded through an end of the intracorporeal device 36 at a hole 38. The anchor point is formed by crimping a piece of metal to the wire and trimming off the excess wire, so that the crimped-on metal comprises the terminal end of the wire. This metal end also provides a radiopaque marker for fluoroscopic visualization of the device.

After the wire 34 is threaded through the hole 38 on one end of the device, the wire is pulled with sufficient force to bury the anchor fixedly into the coating of the intracorporeal device. The wire 34 is then looped around to form the double loop configuration 32. The second free end is also inserted under the coating and the anchor is buried in the coating to fix the anchor. In this manner, the ends of the wire are inserted under the coating of the intracorporeal device 36.

FIG. 3 illustrates the deployment of the implant assembly 30 within a narrowing vessel. The arrow 39 shown in FIG. 3 indicates the direction of blood flow. After being released into the vessel, the wire loop 34 will contact the inner surface 40 of the wall of the vessel 42. Depending upon the configuration of the implant assembly 30 and the inner diameter of the vessel 42, this contact may occur immediately upon deployment. Alternatively, the implant assembly can be configured so that the wire 34 of the implant assembly 30 does not initially contact the inner surface 40 of the vessel 42 but instead travels down the narrowing vessel until, at some point, the vessel narrows to such an extent that the wire loop 34 makes contact with the inner surface 40 of the vessel 42. Depending upon the compliance of the vasculature and the wire loop 34 of the implant assembly 30, the wire structure may compress radially inward or bow backwards as an interference fit is created. Or, depending upon the compliance of the wire comprising the implant assembly, the anchor structure 42 may yield, permitting the implant assembly 30 to travel further downstream. The implant assembly 30 will ultimately reach a point in the narrowing vessel 42 at which an interference fit between the wire loop 34 and the vessel will cause the implant assembly to lodge and to be held in place against any further movement.

An alternate method of anchoring an implant assembly 30 is based upon the principle of causing the intracorporeal device to lodge at a furcation in a vessel of a patient. As an example, the pulmonary artery, which originates in the right ventricle, divides into the right and left pulmonary artery branches, one directed to each lung. These arteries divide and then subdivide, eventually to send arteries to all of the bronchopulmonary segments that form the different lobes of each lung. The pulmonary arterial vessels decrease in diameter significantly each time they divide.

The theory underlying the alternate method of anchoring an implant assembly is that the implant assembly, including the wire loops, can travel down a first vessel with the flow of blood, but when the implant assembly reaches a furcation, the implant assembly is too large to fit through either of the smaller branch vessels. The implant assembly thus lodges at the furcation, prevented from moving downstream by being too large and not sufficiently compliant to fit into the branch vessels, and prevented from moving upstream by the flow of blood through the arteries. In one implementation, the implant assembly diameter is equal to or greater than the inner diameter of the first vessel. In this case, the implant assembly is sufficiently compliant so it does not produce an interference fit as it travels down the vessel but does preserve the intended orientation of the implant assembly when it reaches the subsequent furcation. In an alternate implementation, the implant assembly diameter is less than the inner diameter of the arterial vessel such that no particular orientation is actively preserved but the implant assembly is too large and stiff to fit through subsequent branch vessels.

In either case, the implant assembly is configured such that, after a short period of time, e.g. 30 days, the deployment position is further reinforced by tissue overgrowth of the wire loops where they contact the vessel wall. At this point, the dominant fixation mechanism is the tissue to wire connection and the implant assembly cannot be easily removed without risk of damaging the vessel.

Referring to FIG. 4, the implant assembly 30 has been released into a first vessel 49. The implant assembly is free to travel through the first vessel 49 with the flow of blood in the direction indicated by the arrows 51. At a furcation 53, the first vessel 49 divides into smaller vessels 55, 56. Because the implant assembly 30 is substantially larger than the cross-section of any of the smaller vessels 55, 56, the implant assembly cannot proceed any further and lodges at the furcation 53.

Referring now to FIG. 5, a loop structure having a "figure eight" shape is illustrated. More specifically, an implant assembly 31 having a double loop structure 33 includes a wire 35 attached to the intracorporeal device body 37 at an attachment site (not shown). The ends of the wire 35 are inserted under the coating of the intracorporeal device body 37 as described in the previous example.

The purpose of the "figure eight" or double loop structure 33 is to stabilize the intracorporeal device body from rotating or tumbling end-over-end within the vessel, thereby assuring that, in the case of a wireless sensing element comprising the intracorporeal device, a coupling element of the intracorporeal device body remains properly oriented with respect to optimal angles of interrogation via extracorporeal communication and data acquisition devices. The "figure eight" or double loop structure 33 of the disclosed implementation may be approximately 5 cm in length. However, it will be appreciated that the dimensions depend upon the inner diameter of the vessel into which it is being placed within relatively wide tolerances, and that the dimensions of the "figure eight" or double-loop structure 33 can be modified to adapt the device to any particular vessel. According to one aspect of the disclosure, the overall length of the intracorporeal device body plus double-loop structure 33 is at least two times, and, in certain implementations, at least about five times, the diameter of the vessel.

Figure 6:
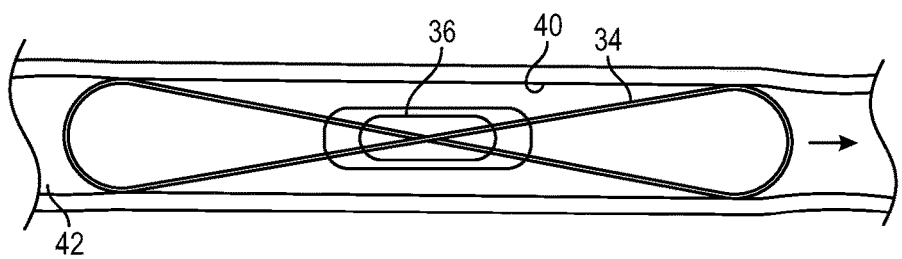
FIG. 6 is a cutaway view of a vessel showing the implant assembly of FIG. 5 fixed therein.

Referring to FIG. 6, upon deployment of the implant assembly 31 according to a first method, the implant assembly 31 is anchored by an interference fit between the wire 35 and the inner surface 41 of the wall of the vessel 43. The arrow 51 indicates the direction of blood flow.

Figure 7:
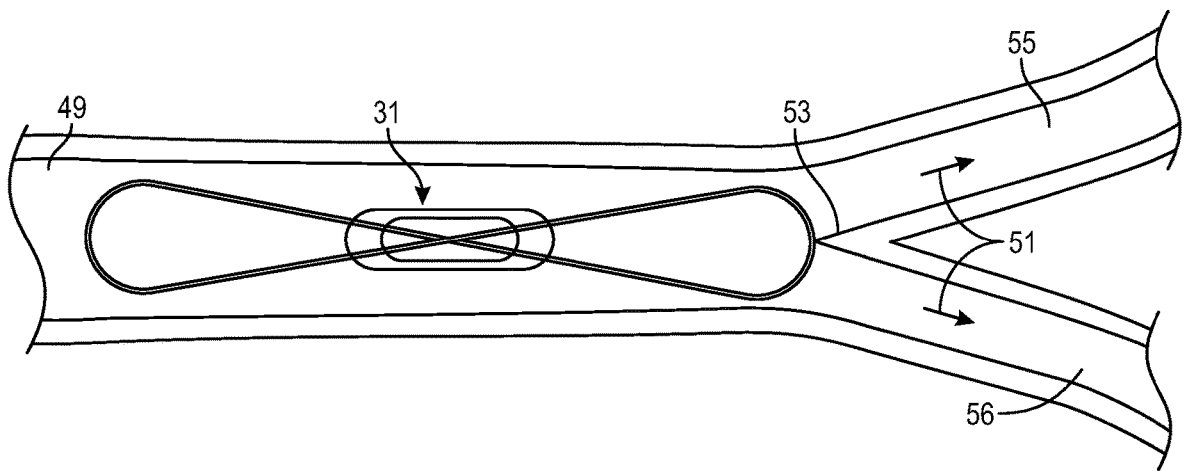
FIG. 7 is a cutaway view of a pulmonary arterial vessel showing the implant assembly of FIG. 5 fixed therein.

FIG. 7 illustrates an alternate method of anchoring the implant assembly 31, in which the implant assembly 31 is deployed, e.g., into a first pulmonary arterial vessel 49 having a cross-section on the order of the cross-section of the implant 10 assembly. The implant assembly thus travels through the first vessel 49 in the direction of blood flow, indicated by the arrows 51. At a furcation 53, the first vessel 49 divides into smaller vessels 55, 56. Because the cross-section of the implant assembly 31 is substantially larger than the cross-section of either of the smaller vessels 55, 56, and not sufficiently compliant to deform further the implant assembly lodges at the furcation 53.

In the illustrated example, the opposed loop structure 33 of the implant assembly 31 is constructed of a single wire. However, it will be understood that the opposed loop structure 33 can be constructed of more than one wire.

In alternative implementations shown in FIGS. 8, 9, 12, and 13, the structure includes a plurality of wire loops 44 encircling an intracorporeal device 46. The wire 48 is threaded from end to end in a circular fashion, through one or more holes 50 located on each end of the intracorporeal device, to form the loops. Upon completion of the loop structure, the free end of the wire is used to create another anchor as described above. The second free end is then pulled back into the coating with sufficient force to bury the second anchor fixedly in the coating. In one implementation, the location of the second anchor lies on the opposite side of the intracorporeal device from the first anchor. This configuration is useful in order to position anchors away from a sensing or actuating element and/or to provide a means for determining the orientation of the device when viewed via fluoroscopic means. The wire loops are then arranged by mechanical means to create wire members that are substantially evenly distributed radially around the longitudinal axis of the intracorporeal device.

Figure 8:
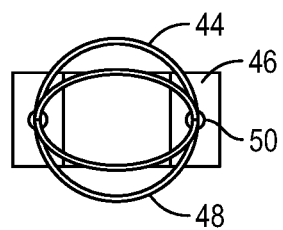
FIG. 8 is a top view of a third embodiment of an implant assembly according to the present disclosure, the implant assembly having two opposed wire loops.
Figure 9:
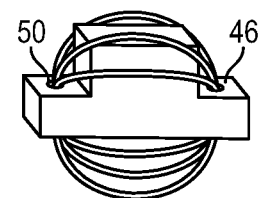
FIG. 9 is an isometric view of the implant assembly of FIG. 8.
Figure 12:
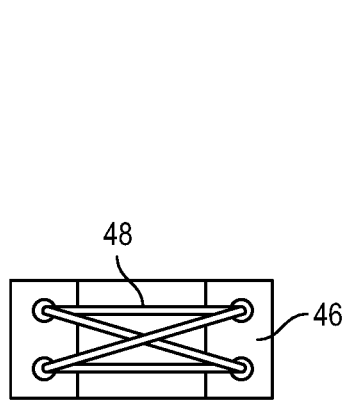
FIG. 12 is a top view of a fourth embodiment of an implant assembly according to the present disclosure, the implant assembly having opposed wire loops.
Figure 13:
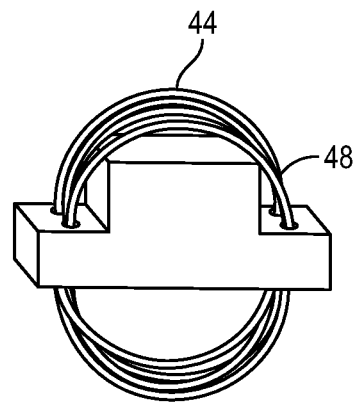
FIG. 13 is an isometric view of the implant assembly of FIG. 12.

The wire loops may be attached to the intracorporeal device 40 by threading through one hole 50 located near the edge of the device 46 as referenced to the longitudinal axis of the device 46, as shown in FIG. 8. Alternatively, the wire loops may be attached to the intracorporeal device 46 by threading through multiple holes 50 located near each edge of the device 46, as shown in FIG. 12.

Figure 10:
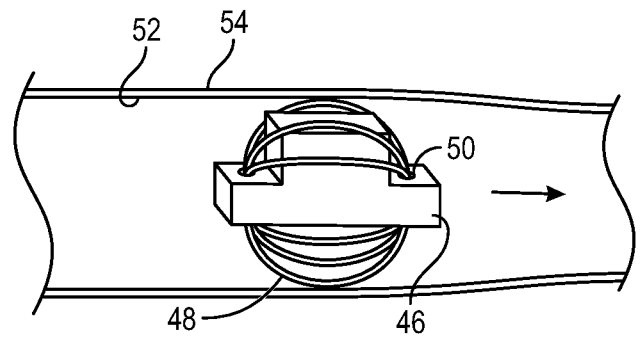
FIG. 10 is a cutaway view of a vessel showing the implant assembly of FIG. 8 fixed therein.
Figure 11:
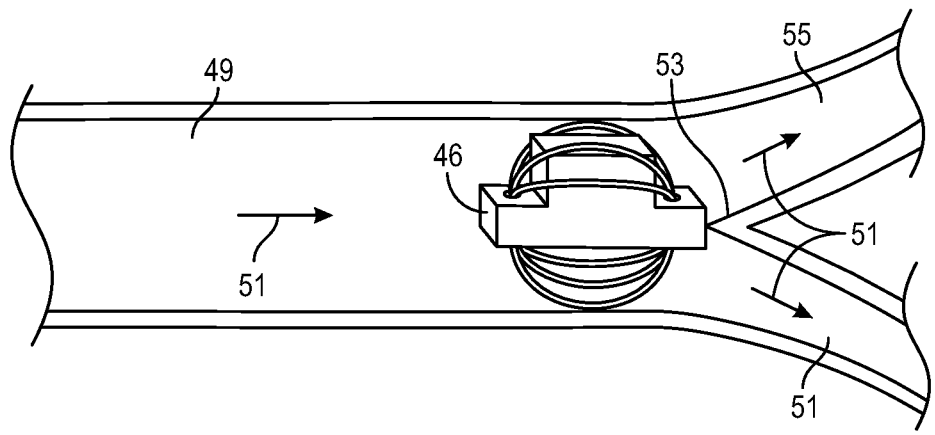
FIG. 11 is a cutaway view of a pulmonary arterial vessel showing the implant assembly of FIG. 8 fixed therein.
Figure 14:
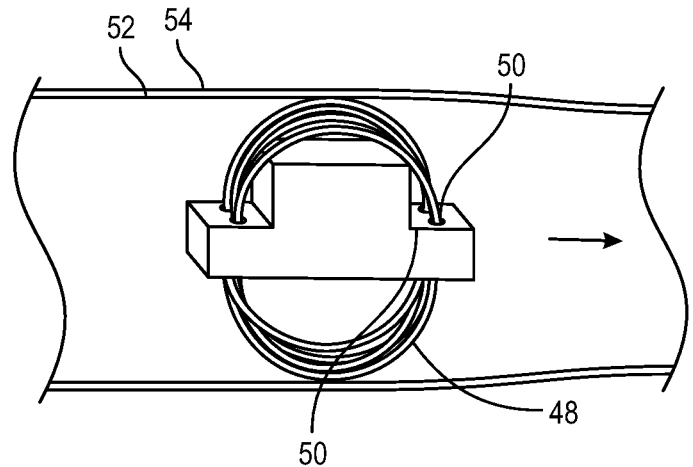
FIG. 14 is a cutaway view of a vessel showing the implant assembly of FIG. 12 fixed therein.
Figure 15:
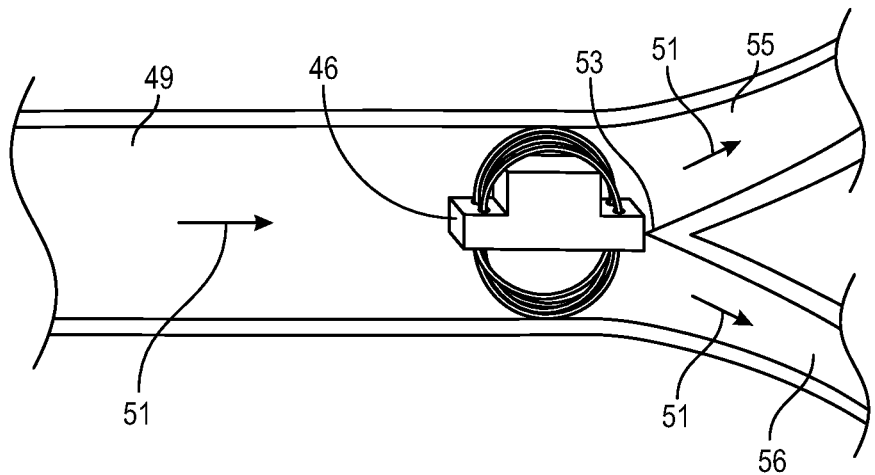
FIG. 15 is a cutaway view of a pulmonary arterial vessel showing the implant assembly of FIG. 12 fixed therein.

The implant assemblies of FIGS. 8, 9, 12, and 13 may be deployed according to either of the two methods described above. The implant assemblies can be configured so that they are anchored by an interference fit between the implant assemblies and the walls 52 of the vessel 54, as shown in FIGS. 10 and 14 and described previously. Or the implant assemblies can be configured so that they are allowed to travel down a vessel and lodge at a furcation as previously described. The arrows 51 shown in FIGS. 10, 11, 14, and 15 indicate the direction of blood flow.

Figure 35:
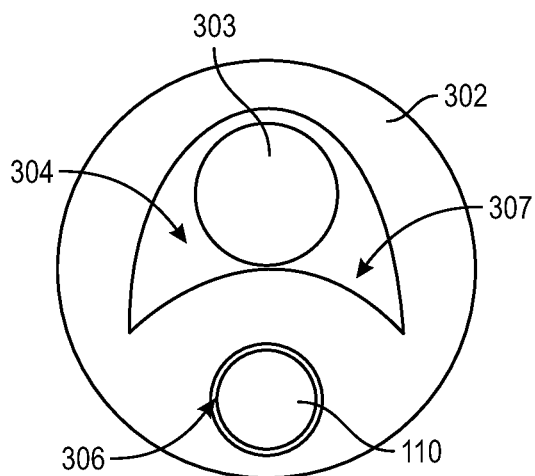
FIG. 35 is a cross-section view of the sheath of FIG. 34 including a delivery catheter and a guidewire disposed therein.
Figure 36:
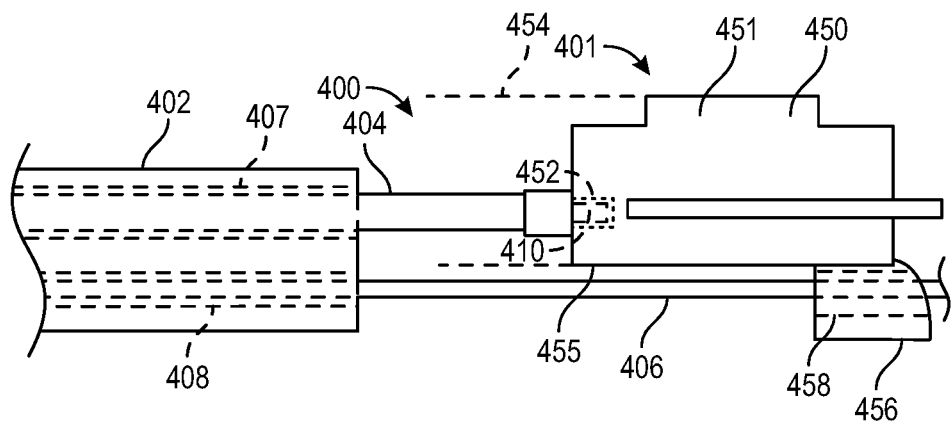
FIG. 36 is a side elevation view of a distal portion of a delivery system including an intracorporeal device.
Figure 37:
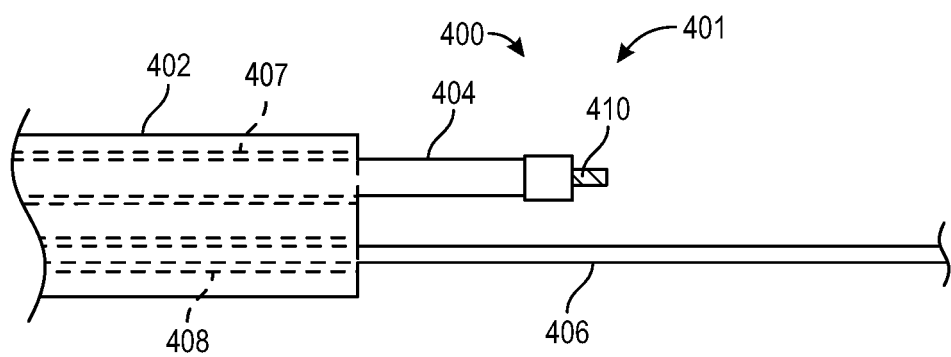
FIG. 37 is a side elevation view of the distal portion of the delivery system of FIG. 36 excluding the intracorporeal device.

Referring now to FIGS. 35-37, an implant assembly 130 includes an intracorporeal device 131, an elongated "figure eight" wire loop 132, and a pair of wing-like wire loops 134. The wing-like wire loops 134 have a longest dimension in a plane orthogonal to the longitudinal axis of the vessel. This longest dimension is, within wide tolerances, on the order of the vessel inner diameter into which the implant assembly 130 is to be introduced, so as to permit the implant assembly to travel down the blood stream until it lodges at a furcation. The "figure eight" wire loop 132 has a length which is greater than the diameter of the vessel into which the implant assembly 130 is to be introduced so as to prevent the implant assembly from flipping end-to-end within the vessel. The length of the "figure eight" wire loop 132 may be at least twice the diameter of the vessel into which the implant assembly 130 is to be introduced, and the length of the "figure eight" wire loop 132 may be approximately five times the diameter of the vessel. This feature is useful to maintain a desired orientation of the implant assembly 130 with respect to the fluid flow within the vessel. In certain implementations, the "figure eight" wire loop lies in a plane, and the wing-like wire loops are oriented substantially perpendicular to the plane defined by the wire loops.

B. Radial Wire Array Structures

Figure 16:
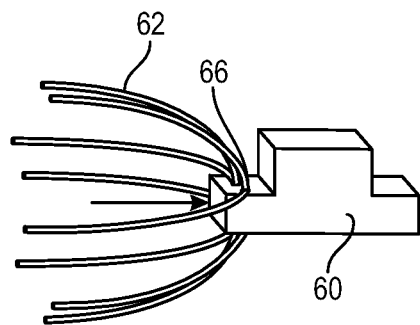
FIG. 16 is an isometric view of a seventh embodiment of an implant assembly according to the present disclosure, the implant assembly having a radial wire array expansible structure.
Figure 17:
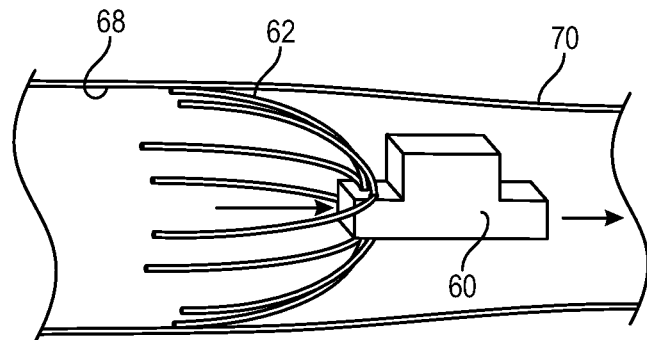
FIG. 17 is a cutaway view of a vessel showing the implant assembly of FIG. 16 fixed therein.
Figure 18:
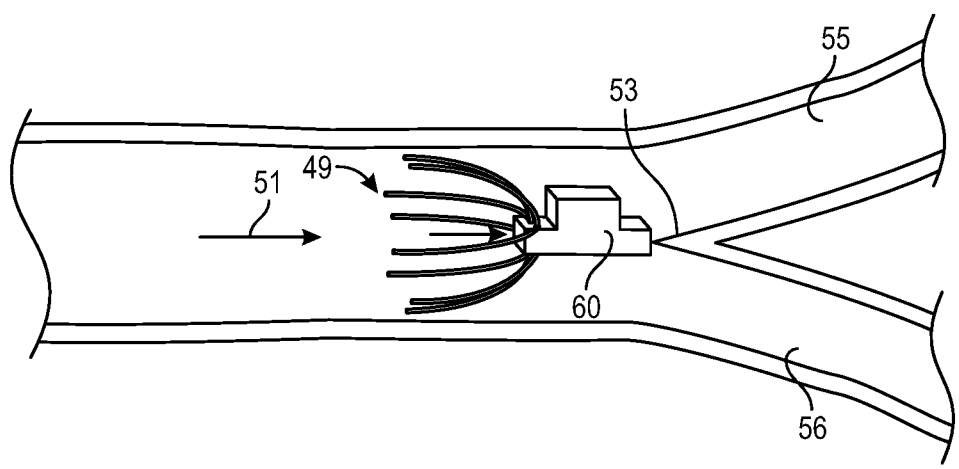
FIG. 18 is a cutaway view of a pulmonary arterial vessel showing the implant assembly of FIG. 16 fixed therein.

Another implant assembly according to this disclosure includes an intracorporeal device and an anchoring structure having a substantially parabolic-shaped profile, as shown in FIGS. 16-18. As illustrated, an implant assembly 58 includes an intracorporeal device 60 and a radial wire array 62, which includes wire members 64. Members 62 may be attached to the intracorporeal device 60 at an anchor point, as described below.

Figure 20:
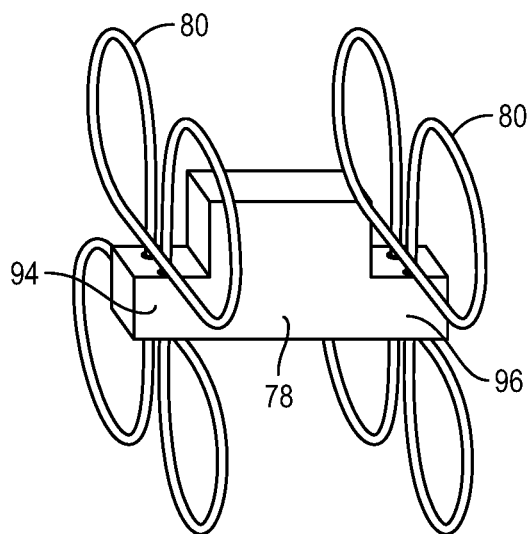
FIG. 20 is an isometric view of a ninth embodiment of an implant assembly according to the present disclosure, the implant assembly having a daisy petal expansible structure on each end of an intracorporeal device.

The radial wire array 62 can be attached to the intracorporeal device 60 by threading the wire members 64 through one hole 66 located near the edge of the intracorporeal device 60, as shown in FIG. 16. Alternatively, the radial wire array 62 can be attached to the intracorporeal device 60 by threading the wire members 64 through two holes 66 located near the edge of the device 60 as shown in FIG. 20. The wire end is press-fit into a coating covering the surface of the device to secure the end. The radial wire array may be formed by crimping a piece of metal at a point substantially midlength of the wire bundle and then threading the wire bundle through a hole near the edge of the intracorporeal device, thus lodging the anchor within the silicone material filling the hole. The anchor secures the end of the radial wire between the surface of the device and the coating covering the surface of the device. The crimped metal anchor provides a radiopaque marker for fluoroscopic visualization of the device.

Figure 21:
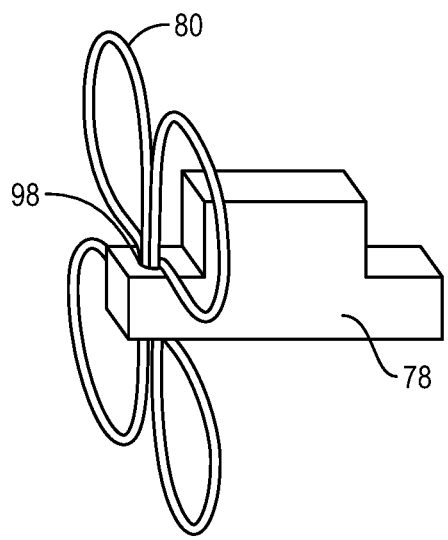
FIG. 21 is an isometric view of a tenth embodiment of an implant assembly of the present disclosure, the implant assembly having a daisy petal wire expansible structure.
Figure 22:
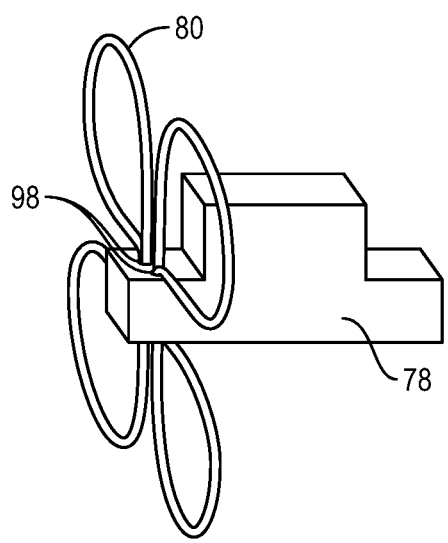
FIG. 22 is an isometric view of an eleventh embodiment of an implant assembly according to the present disclosure, the implant assembly having a daisy petal wire expansible structure.

Upon deployment of the implant assembly, the implant assembly can be anchored either by an interference fit between the radial wires and the walls of the vessel, as shown in FIG. 21, or by traveling within a vessel until the implant assembly lodges at a furcation, as shown in FIG. 22.

In one implementation, the radial wire array is self-supporting, as a result of the physical properties of the material. Alternatively, the radial wire array may include a mechanical expansion structure to support the array to expand and contact the vessel wall. For example, a catheter balloon may be inflated to cause a wire structure to attain and maintain an expanded configuration.

The intracorporeal device 60 can be positioned outside a radial wire array 62 so that one end 72 of the intracorporeal device 60 is fixed to a point at or near the apex of the radial wire array 62, as shown in FIG. 16. The intracorporeal device 60 can also be positioned inside the radial wire array so that one end of the device is fixed to a point at or near the apex of the radial wire array, as shown in FIG. 17. In another implementation, the intracorporeal device may have two radial wire arrays 62 attached to the intracorporeal device 60 so that one end of the intracorporeal device is attached to the apex on the exterior of one of the radial wire arrays and the opposing end of said device is attached to the apex on the interior of the second radial wire array, as shown in FIG. 18.

C. Daisy Petal Structures

Figure 23:
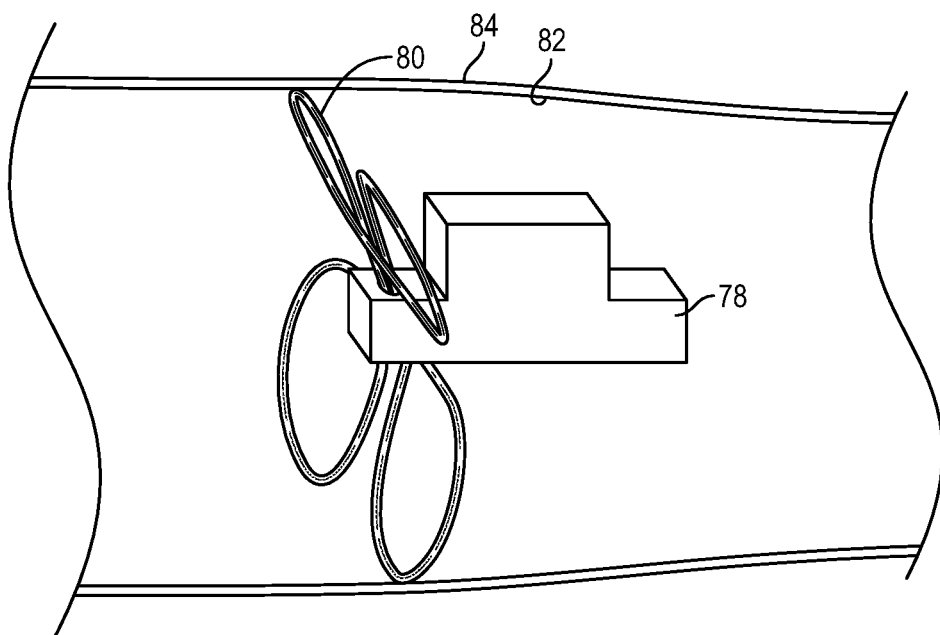
FIG. 23 is a cutaway view of a vessel showing the implant assembly of FIG. 19 fixed therein.
Figure 24:
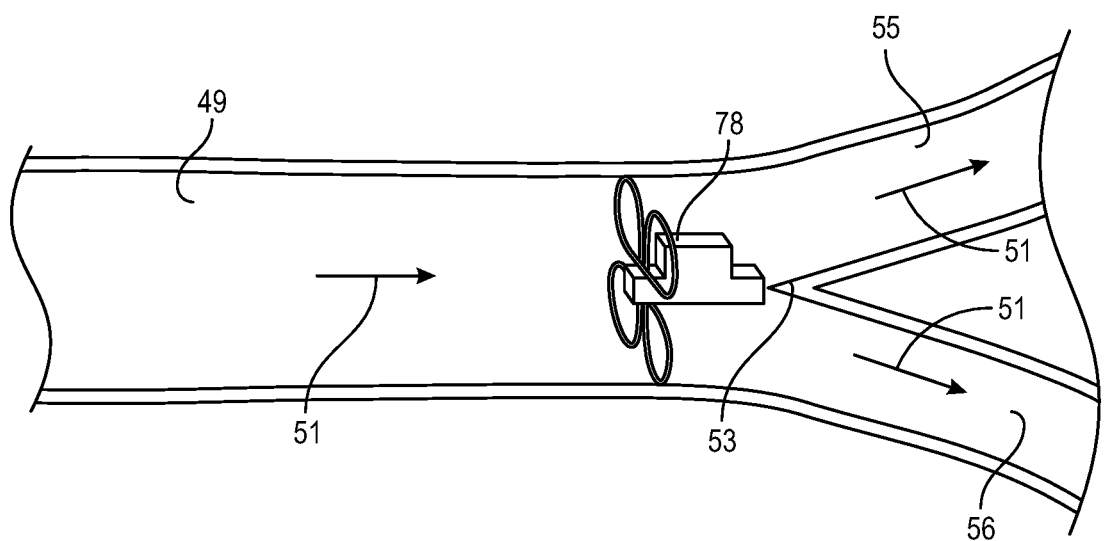
FIG. 24 is a cutaway view of a pulmonary arterial vessel showing the implant assembly of FIG. 19 fixed therein.

An implant assembly according to another aspect of this disclosure includes an intracorporeal device and an anchoring structure having a daisy petal shape, as shown in FIGS. 19-22. The implant assembly 76 includes an intracorporeal device 78 and a daisy petal wire structure 80, which contacts the inner surface 82 of the wall of the vessel 84, as shown in FIG. 23. The implant assembly of this implementation can be anchored by an interference fit between the implant assembly and the walls of the vessel. In the alternative, the implant assembly can be configured, within wide tolerances, to have a diameter on the order of the vessel inner diameter into which the implant assembly 130 is to be introduced, so as to permit the implant assembly to travel down the blood stream until it lodges at a furcation, as shown in FIG. 24. The arrows 51 shown in FIGS. 23 and 24 indicate the direction of blood flow.

Figure 19:
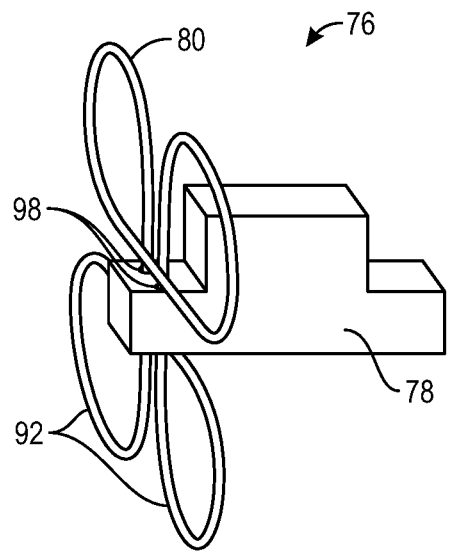
FIG. 19 is an isometric view of an eighth embodiment of an implant assembly according to the present disclosure, the implant assembly having a daisy petal wire expansible structure.

The daisy petal wire structure 80 is positioned so that the structure lies in a plane normal to a longitudinal axis of the intracorporeal device 78. The daisy petal wire structure 80 may be constructed of a single wire or of a plurality of wires. As shown in FIGS. 19, the daisy petal wire structure 80 includes a plurality of lobes 92. The structure may have either an even or an odd number of lobes. As shown in FIG. 20, the intracorporeal device 78 may have two daisy petal wire structures 80 attached to the device on opposing ends 94, 96 and located along the longitudinal axis 90.

The daisy petal wire structure 80 may be attached to the intracorporeal device 78 by threading through a single hole 98 located near the edge of the device 78, as shown in FIG. 21. Alternatively, the daisy petal wire structure 80 may be attached to the intracorporeal device 78 by threading through two holes 98 located near the edge of the device 78, as shown in FIGS. 19 and 22.

In one implementation, the daisy petal wire structure 80 is attached to the intracorporeal device at an anchor point. The anchor is made by crimping a piece of metal to the wire and trimming off the excess wire, so that the crimped-on metal comprises the terminal end of the wire. This metal end also provides a radiopaque marker for fluoroscopic visualization of the device. The wire is threaded through the hole or holes on one end of the intracorporeal device and the wire is pulled with sufficient force to bury the anchor fixedly into the coating. The wire is then threaded from top to bottom in a circular fashion, through the hole or holes located on the end of the intracorporeal device, to form the daisy petal structure. Upon completion of the daisy petal structure, the free end of the wire is used to create another anchor. The second free end is then pulled back into the coating with sufficient force to bury the second anchor fixedly in the coating. The wire loops are then arranged by mechanical means to create wire members that are substantially evenly distributed radially around the longitudinal axis of the intracorporeal device.

D. Delivery Systems and Methods

Figure 25:
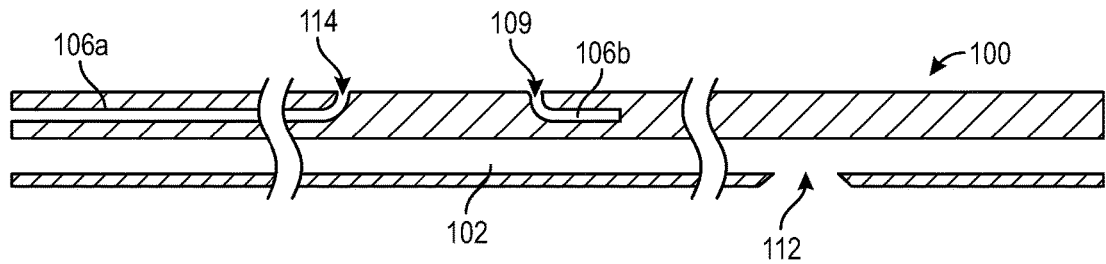
FIG. 25 is a side cross-sectional view of a first embodiment of a delivery apparatus according to the present disclosure.
Figure 26:
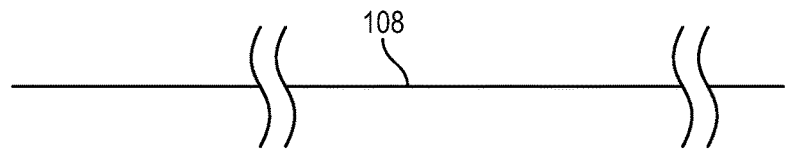
FIG. 26 is a side view of a tether wire of the delivery apparatus of FIG. 25.
Figure 27:
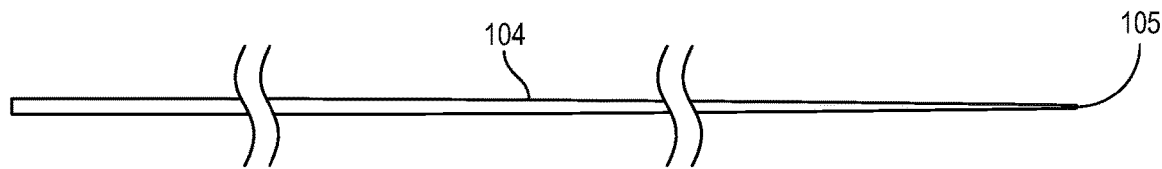
FIG. 27 is a side view of a core wire of the delivery apparatus of FIG. 25.
Figure 28:
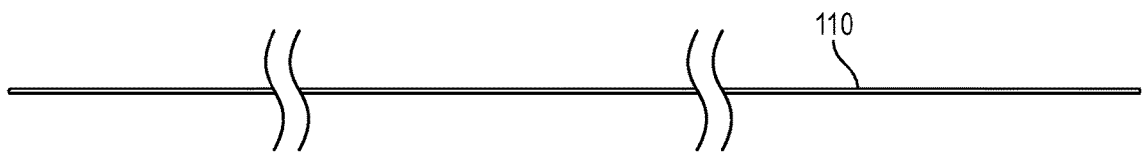
FIG. 28 is a side view of a guidewire of the delivery apparatus of FIG. 25.
Figure 33:
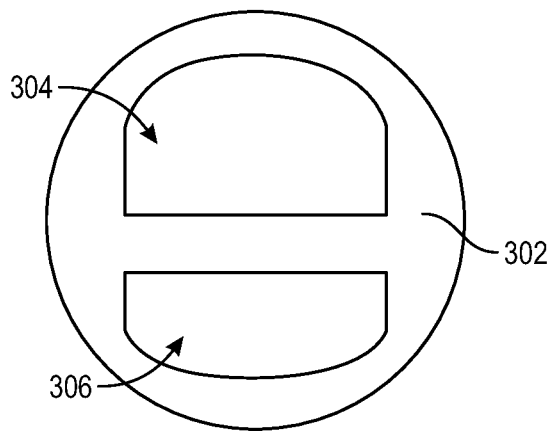
FIGS. 33-34 are cross-sectional views of sheaths that may be used in the delivery system of FIG. 31.

This disclosure further provides a delivery system for securing, delivering, and deploying an implant assembly having an anchoring mechanism coupled to an intracorporeal device. Referring to FIGS. 25-29, the various components of the delivery system are shown individually. As shown in FIG. 25, the delivery apparatus 100 includes a main lumen 102 adapted to accept a core wire 104 (FIG. 27) and a secondary lumen comprising a first section 106A and a second section 106B and adapted to accept a tether wire 108 (FIG. 26). The core wire 104, shown in FIG. 27, provides columnar stiffness to the delivery assembly 100, thereby facilitating advancement of the delivery assembly through the vasculature. Additionally, the core wire 104 also prevents buckling of the delivery assembly 100 when the tether wire is pulled proximally during the implant assembly deployment. The core wire 104 has a decreasing diameter toward its distal end 105, providing gradual decrease in stiffness from the proximal to the distal end of the delivery assembly 100. The tapered core wire 104 can extend past a guidewire aperture 112 in order to reinforce a potential kink point in the delivery apparatus 100 and to facilitate the advancement of the guidewire into the vasculature. The core wire 104 is fixed in the main lumen 102 using adhesive, thermocompression, or any other suitable fixation mechanism. Fixation of the core wire 104 prevents the core wire from being disturbed by the guidewire 110, shown in FIG. 28, when the guidewire 110 enters the main lumen 102 of the delivery apparatus 100 at the guidewire aperture 112 as shown in FIG. 33.

Figure 29:
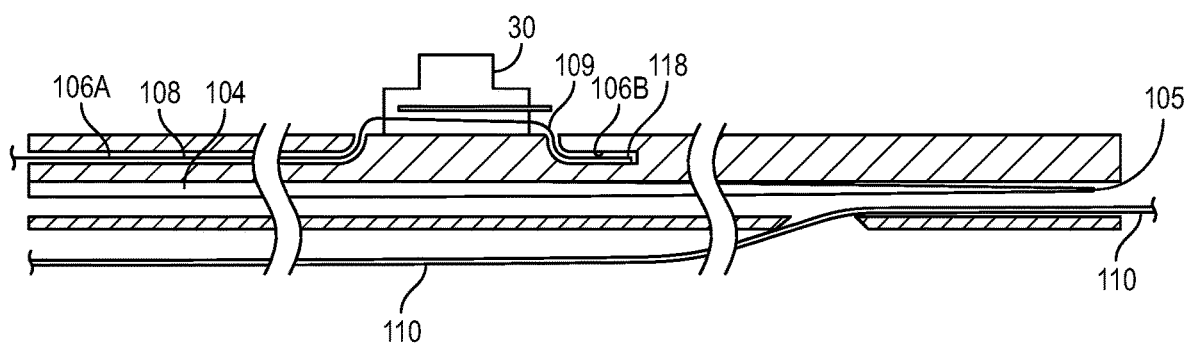
FIG. 29 is a side cross-sectional view of the delivery system of FIG. 25 with an implant assembly coupled thereto.

The tether wire 108, shown in FIG. 26, is slidably positioned within the first secondary lumen portion 106A and exits the first secondary lumen portion at an aperture 114 in the wall of the device. As shown in FIG. 29, the tether wire 108 then passes through the coating of the intracorporeal device 30, exiting on the opposite side of the device. The free end 118 of the tether wire 108 enters the second portion 106B of the secondary lumen at the aperture 109.

Figure 30:
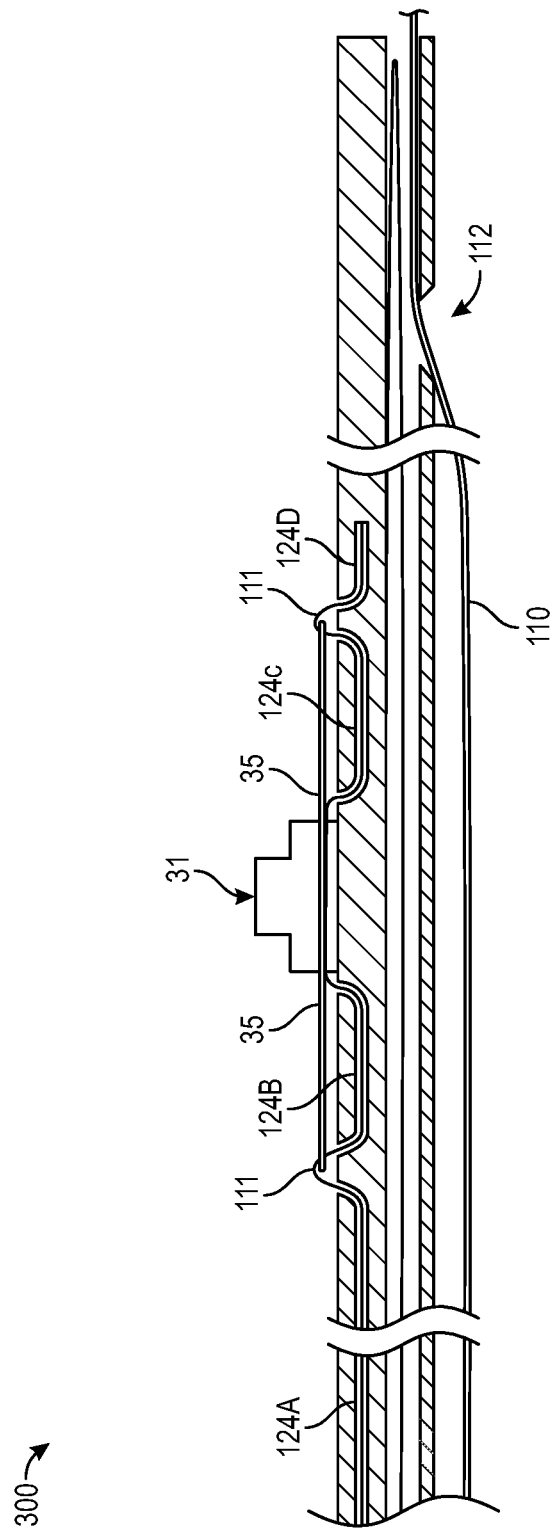
FIG. 30 is a side cross-sectional view of a second embodiment of a delivery system for delivering an intracorporeal device such as that shown in FIG. 5.

FIG. 30 shows an alternate implementation of a delivery apparatus adapted to deploy intracorporeal devices, such as the intracorporeal device 31 of FIGS. 5-7. Because of the length of the wire loops 35 of the intracorporeal device 31, the proximal and distal ends of the loops must be secured to the delivery apparatus so that, when the delivery apparatus curves, the loops will follow the curvature of the delivery apparatus. Toward that end, the secondary lumen of the delivery apparatus of FIG. 30 is divided into four sections 124A-D. The tether wire 108 exits the first section 124A of the secondary lumen and passes over and through wire loops 55 to attach the implant assembly 51 to the delivery apparatus 100. The tether wire then enters the second portion 124B of the secondary lumen. The tether wire then exits the second portion 124B of the secondary lumen and passes through the coating of the intracorporeal device 31. The tether wire then enters the third portion 124C of the secondary lumen. Next, the tether wire exits the third portion 124C of the secondary lumen, passes over the wire loop 35, and enters the fourth section 124D of the secondary lumen.

In yet another configuration, an outer sleeve may be provided to constrain an expansible structure and is slidably positioned over the double lumen tube.

Deployment and fixation of an implant assembly may be accomplished passively by either an interference fit or lodging at a furcation. In one implementation, an implant assembly, including an anchoring structure of sufficient size and/or compliance, is delivered into the vessel and allowed to travel in the blood stream until it lodges at a furcation. After lodging in the vessel, blood flow is maintained due to the configuration of the implant assembly. In another implementation, an implant assembly includes an anchoring structure of sufficient compliance that, upon narrowing of the vessel, produces an interference fit thereby preventing substantially any further progress of the device down the vessel. In a third implementation, the intracorporeal device embolizes without an anchor structure. It could be preferable to eliminate the need for a securing device and to allow the intracorporeal device to reside in a vessel that is small enough to prevent further movement of the intracorporeal device. As an illustration, it is suspected that the small size of the intracorporeal device would have no deleterious effect on lung function due to the redundancy of blood flow in the lungs at the small vessel level.

One method of deploying and fixing an implant assembly according to this disclosure is described below. Access is gained into the vasculature and a vessel introducer is positioned in the access site. The access site for the vessel introducer may be the right internal jugular vein, the subclavian artery, the right femoral vein, or any other suitable access site. A guidewire is placed in the vasculature and positioned across the desired deployment site with the aid of, e.g., a Swan-Ganz catheter, a diagnostic catheter or any other suitable catheter, such catheter being removed after the guidewire is in position.

The delivery system is loaded into the vessel introducer and navigated to the deployment site. The delivery system length can be increased or decreased according to standard practice depending on the access site chosen. In one implementation, the deployment site is a vessel, and may be any artery or arteriole in the pulmonary artery vasculature. Optionally, the implant assembly is oriented to a preferred orientation. Then, the implant assembly is deployed by pulling the tether wire proximally to disengage the implant assembly from the delivery apparatus. Upon deployment, the implant assembly is allowed to travel in the vasculature until an interference fit is produced or it lodges at the next furcation in the vasculature, depending on which mode of fixation is intended. The delivery assembly and guidewire are then removed from the body.

In an alternative implementation of this method, an outer sleeve is provided to constrain an expansible anchor structure so that sliding the outer sleeve proximally allows expansion of the expansible anchor structure. The anchor structure is allowed to expand and the implant assembly travels down the vessel until an interference fit is produced or it lodges at the next furcation in the vasculature, depending on which mode of fixation is intended. The delivery assembly and guidewire are then removed from the body.

For the purpose of illustration, the pulmonary artery is selected as the deployment site for an intracorporeal device. In this example, considerations relevant to the placement of a pressure sensor are disclosed. Other intracorporeal devices could be positioned in alternate locations via modifications to the examples disclosed in this document, such locations and methods being obvious to one skilled in the art in light of the disclosure provided herein. To deploy an implant assembly into a pulmonary arterial vessel, the right femoral vein is chosen as the access site. The user gains access to the femoral vein via transcutaneous puncture or cut-down. A vessel introducer is placed in the site. A Swan-Ganz or guiding catheter is maneuvered into the pulmonary artery. The path to the pulmonary artery is as follows: the femoral vein leads to the inferior vena cava. From the inferior vena cava, the catheter travels through the right atrium to the right ventricle and, finally, to the pulmonary artery. At this point, the right or left branch of the pulmonary artery is selected, and the Swan-Ganz or guiding catheter is positioned in the descending branch of either the right or left pulmonary artery. A guidewire is placed at the deployment site, and the Swan-Ganz or guiding catheter is removed. At this point, the delivery catheter is loaded over the proximal end of the guidewire. Optionally, a guiding catheter can be loaded over the proximal ends of the guidewire and delivery catheter to a point where the distal end of this guiding catheter is located immediately proximal to the implant assembly on the delivery catheter. The delivery catheter (and, optionally, guiding catheter) is tracked over the guidewire to the deployment site. The tether is pulled proximally to disengage the implant assembly from the delivery apparatus.

The lung can be divided into three zones depending on the relationship between the pulmonary artery pressure, alveolar pressure, and pulmonary venous pressure. In Zone 1, the uppermost portion of the lung, the alveolar pressure is greater than that of either the pulmonary artery or the pulmonary vein, causing collapse of the vessel during each respiratory cycle. (Zone 1 conditions do not normally occur in humans.) In Zone 2, the alveolar pressure is less than the pulmonary artery pressure and greater than the pulmonary venous pressure leading to a state of partial vessel collapse. However, in Zone 3, at the bottom of the lungs, all blood vessels remain fully open during the entire respiratory cycle because of the fact that both the pulmonary artery and venous pressures are greater than the alveolar pressure. The implant assembly is released into the descending branch of either the right or left pulmonary artery because this will cause the intracorporeal device to lodge in Zone 3 of the lungs. It is not known whether vessel collapse would cause any deleterious effect on the pressure measured by the sensor, but devices in accordance with the present disclosure eliminate this unknown by positioning the sensor in a location where the possibility of this phenomenon is minimized.

E. Delivery Systems Including External Sheaths

As previously discussed, the general process for implanting intracorporeal devices, such as those described herein, includes identifying a deployment site for the device and gaining access to vasculature corresponding to the deployment site, such as by a transcutaneous puncture or cut-down. A Swan-Ganz or similar guiding catheter may then be inserted through the access point and delivered to the deployment site. A guidewire, such as the guidewire 110 illustrated in FIGS. 28-29 may then be inserted through the guiding catheter to the deployment site. Once the guidewire is properly placed, the guiding catheter may be removed and a proximal end of the guidewire may be inserted into a delivery catheter of a delivery apparatus, such as illustrated in FIGS. 29-30. The delivery catheter, which is coupled to the intracorporeal device to be implanted, may then be translated along the guidewire such that the intracorporeal device is delivered to the implantation location. Once properly positioned, the intracorporeal device may be deployed as previously described in this disclosure, such as by withdrawing a tether wire that couples the intracorporeal device to the delivery catheter.

In implementations according to this disclosure, an additional sheath or catheter may be disposed about each of the delivery catheter and the guidewire. Such a sheath provides various benefits. For example, and without limitation, the sheath may provide additional protection during insertion of the delivery catheter. The sheath may also provide multiple lumens that may be used to inject contrast media or obtain pressure measurements. A lumen of the sheath may also be used to direct other tools to adjust, reposition, or rewire the intracorporeal device during the deployment process. In certain implementations, the sheath may also be used to provide a proximal "stop" for the intracorporeal device to reduce the likelihood of migration of the intracorporeal device during deployment.

Figure 31:
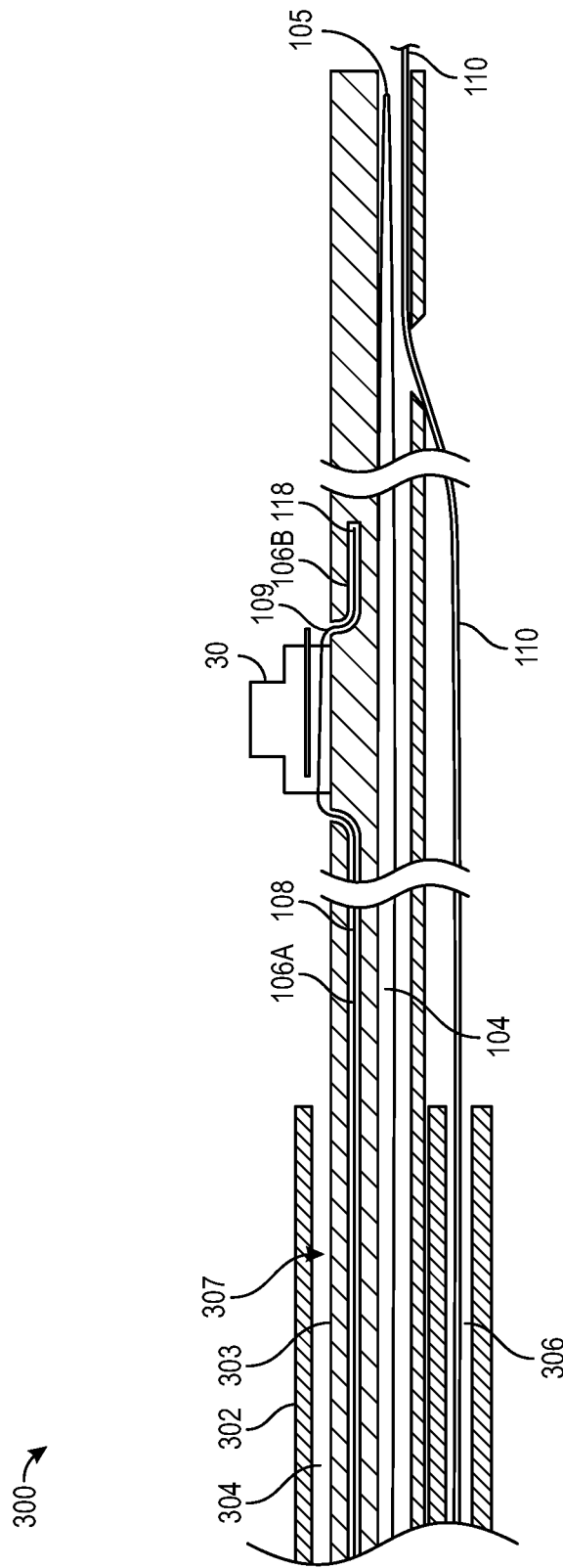
FIG. 31 is a side cross-sectional view of a distal portion of a third embodiment of a delivery system for delivering an intracorporeal device such as that shown in FIG. 5.

Referring to FIG. 31, a delivery system 300 for delivery of an intracorporeal device 30 is provided. In general, the system 300 includes the system 100 illustrated in FIGS. 25-29 disposed within a sheath 302 that extends over a substantial length of each of the delivery catheter 303 and the guidewire 110. Accordingly, unless otherwise indicated, the previous discussion regarding the delivery system of FIGS. 25-29 and its components are applicable to the following description.

As illustrated in FIG. 31, in certain implementations the sheath 302 may define multiple, separate lumens such as a delivery catheter lumen 304 and a guidewire lumen 306. In other implementations, the sheath 302 may instead include a single lumen through which both of the delivery catheter 303 and the guidewire 110 pass. In still other implementations, the sheath 302 may define more than two lumens to facilitate the insertion of additional tools or to otherwise provide additional channels between a hub of the delivery system (described below in more detail in the context of FIG. 32) and the deployment location.

In addition to facilitating delivery of the intracorporeal device 30, the lumens of the sheath 302 may also be used to provide other functionality. For example, and without limitation, one or more lumens of the sheath 302 may be used to inject fluids, such as contrast media, adjacent the deployment location of the intracorporeal device 30 to enable more accurate monitoring of the delivery process using fluoroscopy or similar methods. One or more lumens of the sheath 302 may also be used as conduits from which pressure measurements may be obtained. The pressure measurements may be utilized to calibrate the intracorporeal device 30. Regardless of the additional functionality to be provided, lumens of the sheath 302 for providing such functionality must generally have a sufficient cross-sectional area to allow fluid communication between the deployment site and a hub 310 (shown in FIG. 32 and discussed below in more detail) of the delivery system 300. So, for example, a lumen for providing additional functionality may be separate and independent of any lumen containing the delivery catheter 303 and/or the guidewire 110. Alternatively, if a lumen contains one, or both, of the delivery catheter 303 and the guidewire 110, the lumen may be oversized such that excess cross-sectional area is provided for the additional functionality. For example, the delivery catheter lumen 304 may have a cross-sectional area greater than that of the delivery catheter 303 such that an annular volume 307 is defined between the delivery catheter 303 and the wall defining the delivery catheter lumen 304. The hub 310 may then include a port or similar access point in fluid communication with the annular volume 307 to permit injection or removal of fluid, insertion of tools, measurement using various gauges, or other similar functionality requiring a path between the exterior of the hub and the deployment location.

For purposes of this disclosure, a lumen for providing functionality other than receiving the delivery catheter and/or the guidewire is referred to as an "auxiliary lumen". Accordingly, an auxiliary lumen may correspond to a lumen that is separate and distinct from the delivery catheter lumen and the guidewire lumen or may refer to the delivery catheter lumen and/or the guidewire lumen when the delivery catheter lumen and/or the guidewire lumen are oversized to accommodate both the delivery shaft/guidewire and any additional volume required for performing the additional functionality.

Figure 34:
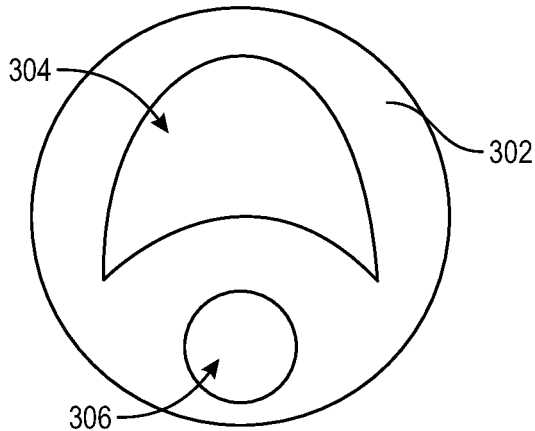

Examples of sheaths in accordance with the present disclosure are illustrated in FIGS. 33-34, which each illustrate cross-sections of sheaths 302 in accordance with the present disclosure. As shown, each of the sheaths 302 illustrated in FIGS. 33-34 include a delivery catheter lumen 304 and a guidewire lumen 306. In the implementation of FIG. 33, each of the delivery catheter lumen 304 and the guidewire lumen 306 are substantially semi-circular in shape. In contrast, the sheath 302 of FIG. 34 includes a crescent-shaped delivery catheter lumen 304 and a circular guidewire lumen 306. Although each of FIGS. 33 and 34 include two separate lumens, sheaths in accordance with the present disclosure may include one or more lumens. Also, while each of the lumens of the sheaths are intended to receive one of the delivery catheter 303 and the guidewire 110, the delivery catheter 303 and the guidewire 110 may share a single lumen. Moreover, the sheath 302 may include multiple lumens within which neither of the delivery catheter 303 and the guidewire 110 is disposed. Such auxiliary lumens may be used to facilitate delivery of other wires, catheters, tools, and the like, or may provide additional fluid pathways through the delivery system 300.

The sheath 302 may be formed from various materials including one or more of biocompatible polymers and metals. For example, in certain implementations, the sheath 302 may be formed from an extruded polymer. In other implementations, the sheath 302 may include polymer or metallic structures embedded within a polymer matrix. For example, a braided wire formed of a biocompatible metal (such as nitinol or stainless steel) may be embedded within a matrix of nylon, Pebax, or other, biocompatible polymer. Sheaths in accordance with this disclosure may also include one or both of an inner and outer liner layer that may also be formed from a biocompatible polymer or metal. The particular size of the sheath 302 may vary depending on the particular application for which it is used. For example, and without limitation, in one implementation, the sheath may have a size of 5 Fr. One or more radiopaque markers may also be disposed on, embedded within, or otherwise coupled to the sheath 302 and used in conjunction with a fluoroscopy or similar machine to provide increased visibility of the sheath 302 during the implantation.

FIG. 35 illustrates the sheath 302 of FIG. 34 with the delivery catheter 303 and the guidewire 110 disposed within the delivery catheter lumen 304 and the guidewire lumen 306, respectively. As illustrated, the delivery catheter lumen 304 has a cross-section that is substantially larger than that of the delivery catheter 303. Accordingly, an annular volume 307 is defined between the delivery catheter 303 and an inner wall of the delivery catheter lumen 304. The annular volume 307 may be used for, among other things, injecting or extracting fluids (such as contrast media) to or from the deployment location; enabling delivery of additional wires, catheters, tools, or the like to the deployment location; or establishing a tap that may be used to measure pressure or other parameters at the deployment location. For example, pressure measurements may be obtained in connection with calibration of the intracorporeal device 30.

Figure 32:
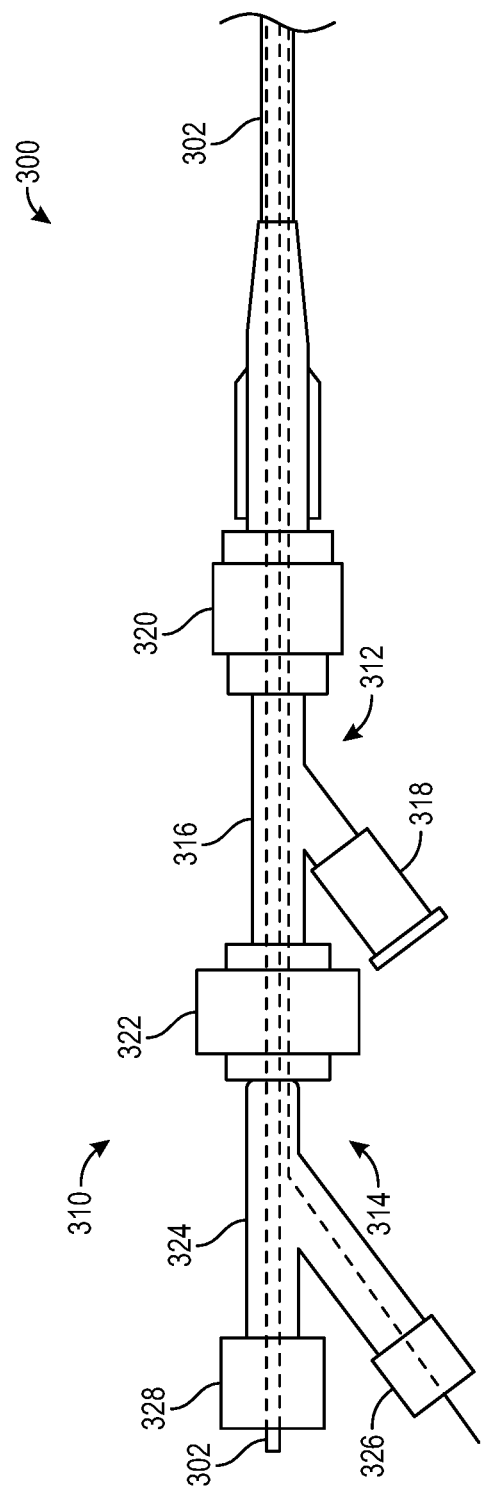
FIG. 32 is a side elevation view of a proximal portion of the delivery system of FIG. 31.

FIG. 32 is a side elevation view of a hub 310 of a delivery system 300 in accordance with the present disclosure. As illustrated, the hub 310 includes each of a distal hub portion 312 and a proximal hub portion 314 which are separable from each other. However, in other implementations, each of the distal hub portion 312 and the proximal hub portion 314 may be integrated into a unitary structure.

As illustrated in FIG. 32, the distal hub portion 312 includes a distal hub body 316 from which the sheath 302 distally extends. The distal hub portion 312 may further include one or more ports, such as port 318, to facilitate various functions. For example, in certain implementations the port 318 may be adapted to enable flushing of the distal hub portion 312. The port 318 may also be adapted to allow injection of contrast media or other fluids for delivery to the deployment location of the intracorporeal device. In other cases, the port 318 may be in fluid communication with the deployment location via one or more lumens of the sheath 302 such that a pressure gauge or similar pressure measurement device may be coupled to the port 318 to measure pressure in the deployment location. In still other cases, the port 318 may be used to insert wires, catheters, tools, or other items for delivery to the deployment location via the sheath 302. As illustrated, the distal hub portion 312 further includes a distal seal 320 and a proximal seal 322. For example, and without limitation, each of the distal seal 320 and the proximal seal 322 may be Tuohy-Borst-type adapters that prevent backflow about instruments inserted therethrough.

As further illustrated in FIG. 32, the proximal hub portion 314 includes a proximal hub body 324 including a first branch 325A for receiving the guide wire 110 and a second branch 325B through which the delivery catheter is inserted. The proximal hub body 324 may further include one or more caps or seals, such as guidewire cap 326 and proximal seal 328.

The method of implementing the hub 310 of FIG. 32 is generally as follows. The intracorporeal device 30 is loaded onto the delivery catheter 303 as previously described in the context of FIGS. 25-30. The loaded delivery catheter 303 is then inserted through the sheath 302 and each of the distal hub portion 312 and the proximal hub portion 314. In implementations in which the sheath 302 includes a delivery catheter lumen 304, insertion of the loaded delivery catheter 303 generally includes passing a proximal end of the delivery catheter 303 into and through the delivery catheter lumen 304.

With respect to the patient, an access point is formed, such as by a transcutaneous puncture or cut-down, and a Swan-Ganz or similar guiding catheter is inserted through the access point of the patient and delivered to the deployment site. The guidewire 110 is then inserted through the guiding catheter such that a distal end of the guidewire 110 is delivered to the deployment site for the intracorporeal device 30. Once the guidewire 110 is properly located, the guiding catheter is removed. Notably, the process of loading the delivery catheter 303 and delivery of the guidewire 110 are separate processes that may occur in any order.

The delivery catheter 303 and hub 310 are then loaded onto the guidewire 110. In general, this process involves inserting a proximal end of the guidewire 110 into a lumen of the sheath 302 (such as the guidewire lumen 306) and passing the delivery catheter 303 and the hub 310 along the guidewire 110 such that a distal end of the delivery catheter 303 is positioned at the deployment location for the intracorporeal device 30. Once so positioned, the intracorporeal device 30 is released from the delivery catheter 303, such as by withdrawing a tether wire 108 coupling the intracorporeal device 30 to the delivery catheter 303. After deployment of the intracorporeal device 30, each of the delivery catheter 303, the sheath 302, and the guidewire 110 may be extracted from the patient.

In implementations in which the intracorporeal device 30 is deployed by withdrawing a tether wire 108, the tether wire 108 friction between the intracorporeal device 30 and the tether wire 108 may result in proximal shifting of the intracorporeal device 30 as the tether wire 108 is withdrawn. To avoid such displacement, the sheath 302 may distally extend such that a distal end of the sheath 302 is adjacent the intracorporeal device 30 when the intracorporeal device 30 is loaded onto the delivery catheter 303. Any proximal shifting of the intracorporeal device 30 would then result in the intracorporeal device 30 abutting the sheath 302, thereby preventing proximal displacement during deployment. Alternatively, the sheath 302 may be configured to be translatable along the guidewire 110 such that prior to deployment of the intracorporeal device 30, the sheath 302 may be distally translated to prevent proximal displacement of the intracorporeal device 30 during deployment.

F. Delivery Systems Including In-Line Delivery Shafts

Previously discussed implementations of the present disclosure generally include an intracorporeal device that is releasably coupled to a distal portion of a delivery catheter. More specifically, the intracorporeal devices are coupled to the delivery catheters by disposing the intracorporeal device adjacent the distal portion of the delivery catheter and then tethering the intracorporeal device to a side of the delivery catheter using a tether wire. The assembly may be then loaded onto a guidewire by inserting a proximal end of the guidewire through a lumen defined by the delivery catheter or a sheath through which the delivery catheter extends.

While side-mounting the intracorporeal device to the delivery catheter enables delivery of the device to a deployment location within the vasculature of a patient, the side-mounted approach has certain limitations. For example, the total width of the delivery system is necessarily limited to no less than the total width of the intracorporeal device, the delivery catheter, and the guidewire. The tether-based approach also requires that the delivery catheter extend substantially beyond the distal end of the intracorporeal device (as illustrated, for example, in FIGS. 29 and 30) to enable fixation of the distal end of the tether to the delivery catheter. In practice, such additional length is generally on the order of 1.25 inches. Accordingly, deployment locations available using the side-mounted delivery method can be limited based on the various imposed dimensional limitations.

Using a tether, as in the previously discussed side-mounted approach, may also present certain issues related deployment accuracy of the intracorporeal device. For example, when withdrawing the tether from the intracorporeal device during deployment, friction between the tether and the intracorporeal device may cause the intracorporeal device to be pulled proximally, shifting the intracorporeal device out of its intended deployment position. Such displacement may also occur as a result of withdrawing the delivery catheter after the intracorporeal device has been released. For example, as the delivery catheter is withdrawn, it may contact the intracorporeal device, knocking the intracorporeal device out of place or proximally pulling the intracorporeal device due to friction between the delivery catheter and the intracorporeal device.

To address the foregoing issues, the present disclosure provides an alternative delivery system for deployment of intracorporeal devices. In contrast to the previously discussed side-mounted approach, the disclosed delivery system instead allows the intracorporeal device to be releasably coupled to a distal end of a shaft. For example, in one implementation, the delivery system includes a delivery shaft having a threaded tip that can be coupled with a corresponding female hole formed in a proximal end of the intracorporeal device. Accordingly, after placement of the intracorporeal device, the delivery shaft may be counter-rotated to unscrew the tip from the hole, thereby releasing the intracorporeal device. As a result, the intracorporeal device and the delivery shaft are maintained in a substantially coaxial arrangement such that their overall width does not exceed that of the intracorporeal device when the intracorporeal device is coupled to the delivery system.

In certain implementations, the overall width of the delivery system is further reduced by including a guidance feature on the intracorporeal device that is shaped to receive the guidewire during delivery and deployment. As a result, the guidewire is maintained in relatively close proximity to the intracorporeal device as compared to side-mounted delivery systems in which the guidewire is passed through a lumen of the delivery catheter.

In addition to reducing the overall size of the delivery system as compared to side-mounted configurations, certain implementations of the end-mounted delivery systems mitigate the potential for migration of the intracorporeal device during deployment. For example, in implementations in which a threaded connection is used between the delivery catheter and the intracorporeal device, deploying the intracorporeal device requires rotation of the delivery catheter but does not generally require proximal pulling of the delivery catheter that may cause movement of the intracorporeal device.

In light of the foregoing, the decreased size of end-mounted delivery systems in accordance with the present disclosure increase the number of possible deployment locations for intracorporeal devices as compared to side-mounted configurations. Moreover, in certain implementations, the accuracy of such deployments is also improved by reducing the amount of proximal pulling of the delivery catheter that is required to deploy the intracorporeal device.

FIGS. 36-37 are side elevation views of a distal end 401 of a delivery system 400 in accordance with the present disclosure. FIG. 36 illustrates the delivery system 400 including an intracorporeal device 450 while FIG. 37 excludes the intracorporeal device 450 for clarity and to illustrate other aspects of the delivery system 400. Although the intracorporeal device 450 is illustrated as being wireless, implementations of the present disclosure may be used in conjunction with wired intracorporeal devices as well.

As illustrated, the delivery system 400 generally includes a sheath 402 through which each a delivery shaft 404 is passed and within which a guidewire 406 may be received. More specifically, during an implantation operation for the intracorporeal device 450, the guidewire 406 may be inserted into a patient such that the guidewire 406 extends from outside the patient to the desired deployment location for the intracorporeal device 450. Accordingly, to deliver the intracorporeal device 450 to the desired deployment location, the delivery system 400 is loaded onto a proximal end of the guidewire 406 and translated along the guidewire 406 until the intracorporeal device 450 is properly located.

The sheath 402 may define one or more lumens. For example, as illustrated in FIGS. 36-37, the sheath 402 includes each of a delivery shaft lumen 407 and a guidewire lumen 408 shaped to receive the delivery shaft 404 and the guidewire 406, respectively. The delivery shaft 404 and the guidewire 406 may alternatively be received by the same lumen. Moreover, the sheath 402 may define additional lumens other than those used to receive the delivery shaft 404 and the guidewire 406.

In certain implementations, one or more lumens of the sheath 402 may be used to provide additional functionality other than or in addition to receiving the delivery shaft 404 and the guidewire 406. For example, and without limitation, a lumen of the sheath 402 may be adapted to enable injection of a contrast media or other fluid to the deployment location. As another example, the lumen may be adapted to enable extraction or sampling of fluid from the deployment location. As yet, another example, a pressure gauge or other sensor device may be coupled to the lumen to monitor or measure physiological parameters, such as blood pressure, at the deployment location. Such additional functionality may be achieved by providing additional lumens other than those adapted to receive the delivery shaft 404 and the guidewire 406. Alternatively, the lumens for receiving the delivery shaft 404 and/or the guidewire 406 may be oversized such that an annular volume about the delivery shaft 404 and/or the guidewire 406 may be used to facilitate the additional functionality.

Similar to the lumen 302, a lumen for providing additional functionality other than receiving the delivery catheter and/or the guidewire is referred to herein as an "auxiliary lumen." Accordingly, an auxiliary lumen may correspond to a lumen that is separate and distinct from the delivery shaft lumen and the guidewire lumen or may refer to the delivery shaft lumen and/or the guidewire lumen when the delivery shaft lumen and/or the guidewire lumen are over-sized to accommodate both the delivery shaft/guidewire and any additional volume required for performing the additional functionality.

In certain implementations, the sheath 402 may be substantially similar to the sheath 302 discussed in the context of FIGS. 31-35. Accordingly, the foregoing discussion regarding the design of the sheath 302 is equally applicable to the sheath 402 of the delivery system 400.

The delivery shaft 404 includes a distal coupling feature 410 adapted to releasably couple with a corresponding proximal coupling feature 452 of the intracorporeal device 450. In the implementation illustrated in FIGS. 36-37, for example, the distal coupling feature 410 of the delivery shaft 404 is a male threaded tip and the proximal coupling feature 452 of the intracorporeal device 450 is a female threaded hole. Accordingly, the delivery shaft 404 is releasably coupled by screwing and unscrewing the distal coupling feature 410 into and out of the proximal coupling feature 452.

When coupled by the distal coupling feature 410 and the proximal coupling feature 452, the delivery shaft 404 and the intracorporeal device 450 are maintained in a substantially coaxial arrangement. More generally, the delivery shaft 404 is maintained within the outer bounds of the intracorporeal device 450 such that, when coupled, the delivery shaft 404 is located within an axial envelope 454 defined by a body 451 of the intracorporeal device 450. Accordingly, the delivery shaft 404 does not increase the total width of the delivery system 400 when coupled to the intracorporeal device 450.

A threaded connection between the delivery shaft 404 and the intracorporeal device 450 is just one example of potential coupling features that may be used to join the delivery shaft 404 and the intracorporeal device 450. Various other coupling mechanisms may be implemented provided the delivery shaft 404 is maintained within the axial envelope 454 defined by the body 451 of the intracorporeal device 451 and the coupling of the delivery shaft 404 to the intracorporeal device 450 is sufficiently robust to maintain the intracorporeal device 450 on the delivery shaft 404. For example, in one alternative implementation, the distal coupling feature 410 and the proximal coupling feature 452 may be coupled by a twist-lock mechanism. In another example implementation, the distal coupling feature 410 may be selectively expandable such that it may be expanded the proximal coupling feature 452 to couple the delivery shaft 404 to the intracorporeal device 450. In yet another example implementation, the distal coupling feature 410 may be magnetically coupled to the proximal coupling feature 452. In such implementations, the delivery coupling feature 410 may include an electromagnet that may be selectively activated or deactivated to retain or release the intracorporeal device 450, respectively. In still another implementation, the distal coupling feature 410 may include a snare or hook shaped to engage and retain the proximal coupling feature 452 such that by extending or expanding the snare or hook, the delivery shaft 404 and the intracorporeal device 405 may be selectively coupled and decoupled.

The term "delivery shaft", as used herein, is intended to refer generally to a flexible elongate body with a distal end that is releasably coupleable to the proximal end of the intracorporeal device 450. In certain implementations, the delivery shaft may be formed from a single wire or strand or may include multiple wires or strands wound or otherwise coupled into a cable. The delivery shaft may be formed from one or more biocompatible materials including, without limitation, one or more of biocompatible polymers (e.g., polyether ether ketone (PEEK), polyvinyl chloride (PVC), polypropylene (PP), polyethylene (PE), polystyrene (PS), nylon, polyethylene terephthalate (PET), polyimide (PA), polycarbonate (PC), acrylonitrile butadiene (ABS), or polyurethane (PU)) or metals (e.g., stainless steel, titanium, steel alloys, and titanium alloys, such as Nitinol). In certain implementations, the delivery shaft may include multiple materials elements. For example, the shaft may include a reinforced braid made of a relatively hard metal or polymer embedded within a relatively flexible polymer body.

As illustrated in FIG. 36, the intracorporeal device 450 may include a guide 456 adapted to receive the guidewire 406. The guide 456 generally provides a passage 458 or channel through which the guidewire 406 may extend. In the illustrated implementation, for example, the guide 456 is disposed on a side of the intracorporeal device 450 near the distal end of the intracorporeal device 450. As a result, the guide 456 extends from a bottom side 455 of the intracorporeal device 450 such that the passage 458 is offset from the body 451 of the intracorporeal device 450. In other implementations, the guide 456 may alternatively be coupled to a top surface, a side surface, a proximal surface, or a distal surface of the intracorporeal device 450 provided the passage 458 is sufficiently offset from the body 451 of the intracorporeal device (e.g., positioned outside the axial envelope 454).

Figure 38:
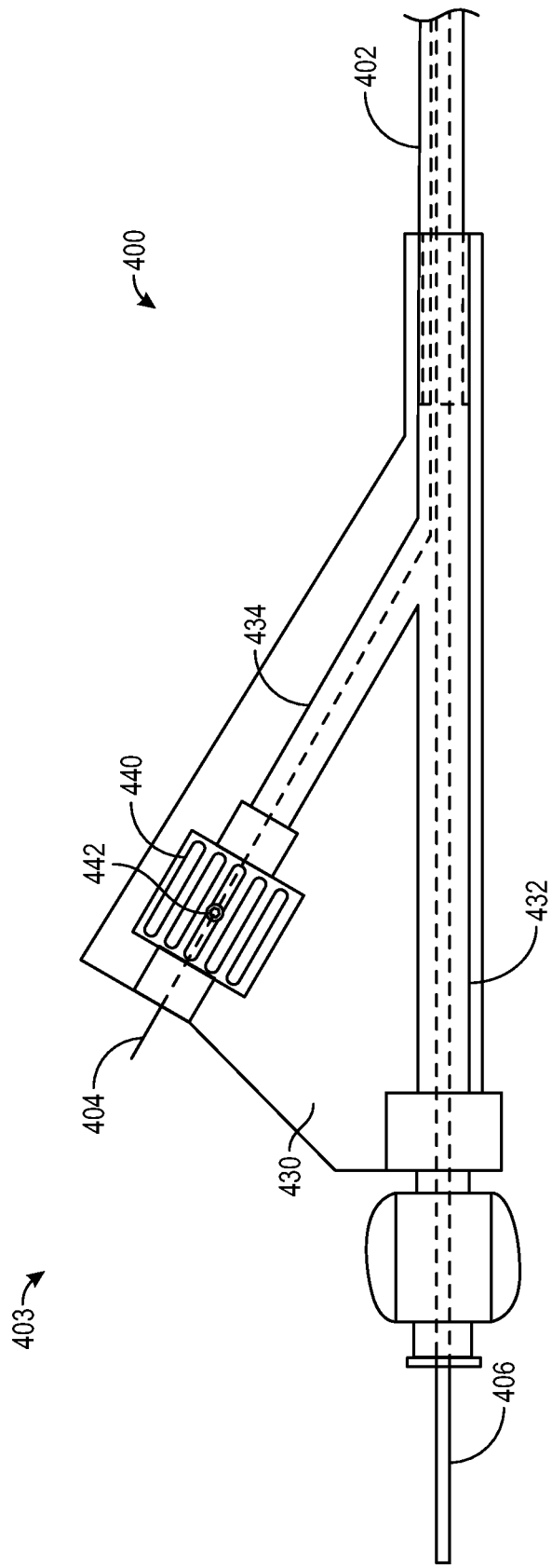
FIG. 38 is a side elevation view of a proximal portion of the delivery system of FIGS. 36-37.

FIG. 38 is a side elevation view of a proximal end 403 of the delivery system 400. The proximal end 403 generally includes a hub 430 adapted to receive and manipulate each of the guidewire 406 and the delivery shaft 404. The sheath 402 of the delivery system 400 is coupled to and extends from a distal end of the hub 430. The hub 430 further includes each of a guidewire passage 432 and a delivery shaft passage 434 shaped to receive and guide the guidewire 406 and the delivery shaft 404, respectively. The hub 430 is arranged in a y-shape such that the guidewire passage 430 extends parallel to the sheath 402 while the delivery shaft passage 432 extends at an angle relative to each of the guidewire passage 434 and the delivery shaft passage 432.

The y-shaped arrangement of the hub 430 is only one arrangement contemplated by the present disclosure. In other implementations, the delivery shaft passage 434 and the guidewire passage 432 may be configured in other arrangements. In other implementations, the hub 430 may also include one or more additional passages adapted to enable insertion of tools, injection or removal of fluids from within the hub 430, flushing of the hub, or various other functions. Moreover, while the hub 430 is illustrated in FIG. 38 as having a substantially unitary construction, in other implementations, the hub 430 may include multiple separate sections that are joined together using appropriate seals and couplings. For example, the hub 430 may include each of a proximal section and a distal section similar to the hub 310 illustrated in FIG. 32.

As previously discussed in the context of FIGS. 36-37, the delivery shaft 404 includes a distal coupling feature 410 in the form of a male threaded tip. Accordingly, the hub 430 is adapted to enable rotation of the delivery shaft 404 to facilitate coupling and decoupling of the delivery shaft 404 from the intracorporeal device 450. As illustrated in the implementation of FIG. 38, for example, the delivery shaft 404 is coupled to a knob 440, such as by a set screw 442, such that rotation of the knob 440 rotates the delivery shaft 404. So, after the intracorporeal device 450 is positioned at the deployment location within the patient, the knob 440 may be rotated to cause the threads of the distal coupling feature 410 to unscrew and ultimately disengage from the intracorporeal device 450.

The knob 440 is one example of a feature of the hub 430 adapted to enable manipulation of the delivery shaft 404 and, in particular, to facilitate disengagement of the delivery shaft 404 from the intracorporeal device 450. In other implementations, the hub 430 may include one or more other features, such as buttons, sliders, knobs, switches, locks, pumps, or the like adapted to manipulate the delivery shaft 404 and/or the distal coupling feature 410 thereof.

Delivery of an intracorporeal device using the delivery system 400 generally includes first inserting the guidewire 406 into the patient. For example, in certain applications an access point is formed, such as by a transcutaneous puncture or cut-down, and a Swan-Ganz or similar guiding catheter is inserted through the access point of the patient and delivered to the deployment site. The guidewire 406 is then inserted through the guiding catheter such that a distal end of the guidewire 406 is delivered to the deployment site for the intracorporeal device 450. Once the guidewire 406 is properly located, the guiding catheter is removed.

Before, during, or after the process of implanting the guidewire 406, the intracorporeal device 450 may be loaded onto the delivery system 400. In general, loading includes one or more of inserting the delivery shaft 404 through the hub 430 and sheath 402 such that the delivery shaft 404 protrudes from a distal end of the sheath 402 and coupling the distal coupling feature 410 of the delivery shaft 404 to the corresponding proximal coupling feature 452 of the intracorporeal device 450. In implementations in which the distal coupling feature 410 is a male threaded tip and the proximal coupling feature 452 is a corresponding female threaded hole, for example, the distal coupling feature 410 of the delivery shaft 404 and the proximal coupling feature 452 of the intracorporeal device 450 may be coupled together by contacting the male threads with the female threads and rotating the delivery shaft 404 such that the threads engage. In certain implementations, such rotation is achieved by rotating a knob or similar feature of the hub 430 to which the delivery shaft 404 is coupled. Accordingly, the loading process may further include coupling the delivery shaft 404 to the knob 440 of the hub 430. As previously discussed, coupling of the delivery shaft 404 to the intracorporeal device 450 may be accomplished using other arrangements of coupling mechanisms other than a threaded connection. In such implementations, the loading process generally includes coupling the delivery shaft 404 to the intracorporeal device 450 according to the specific coupling mechanisms of the implementation. Such coupling may include manipulation of one or more features of the hub 430 adapted to manipulate the coupling feature of the delivery shaft 404 or to otherwise control release of the coupling between the delivery shaft 404 and the intracorporeal device 450.

Once loaded with the intracorporeal device 450, the delivery system 400 is loaded onto the guidewire 406. In general, this process involves inserting a proximal end of the guidewire 406 into a lumen of the sheath 402 (such as the guidewire lumen 408) and passing the delivery catheter 404 and the hub 430 along the guidewire 406 such that a distal end of the delivery shaft 404 is positioned at the deployment location for the intracorporeal device 450. Once so positioned, the intracorporeal device 450 is released from the delivery shaft 404. In the current example, such deployment is achieved by withdrawing the guidewire 406 from the guide 456 of the intracorporeal device 450 (and optionally from the patient entirely) then counter-rotating the delivery shaft 404, thereby unscrewing the distal coupling feature 410 of the delivery shaft 404 and the proximal coupling feature 452 from the intracorporeal device 450. Once fully unscrewed, the intracorporeal device 450 is released from the delivery shaft 404 and the sheath 402, delivery shaft 404, and guidewire 110 may be extracted from the patient, leaving the intracorporeal device 450 in place.

As previously noted, the sheath 402 may be configured to have oversized lumens for receiving the guidewire 406 or delivery shaft 404 or additional lumens adapted to enable one or more of the introduction of additional tools, injection of fluid into the patient, withdrawal of fluid from the patient, obtainment of pressure or other physiological measurements, and similar additional functionality. Accordingly, any such functions may be performed during the course of the delivery of the intracorporeal device 450 with the delivery system 400. For example, during delivery of the intracorporeal device 450, an initial pressure reading may be taken to confirm that the patient is stable and/or that no local irregularities are present at the deployment location of the intracorporeal device 450. As another example, contrast media may be periodically injected through the sheath 402 as the delivery system 400 is moved along the guidewire 406 to confirm (using fluoroscopy or a similar system) the progress of the intracorporeal device 450 and to determine if and when the intracorporeal device 450 is located at its final deployment location.

Unless otherwise stated, terms used herein such as "top," "bottom," "upper," "lower," "left," "right," "front," "back," "proximal," "distal," and the like, are used only for convenience of description and are not intended to limit the scope of this disclosure to any particular orientation.

As for additional details pertinent to the present disclosure, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like, in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

Finally, it will be understood that the embodiments herein have been disclosed by way of example, and that other modifications may occur to those skilled in the art without departing from the scope and spirit of the appended claims.

What is claimed is:

1. An intracorporeal device delivery system, comprising
an intracorporeal device comprising a proximal coupling feature and a device body, wherein the intracorporeal device is a pressure sensor configured to be located and fixed at a deployment site in a vessel;
a delivery catheter comprising a distal coupling feature configured to be coupled to the proximal coupling feature;
a sheath adapted to receive the delivery catheter; and
a lumen provided in at least one of the sheath or delivery catheter, the lumen having a proximal end and a distal end, the distal end proximate to the deployment site, the lumen having a cross-sectional area sufficient and configured to be utilized as a conduit from which calibration pressure measurements are obtained at the deployment site after the distal coupling feature of the delivery catheter is decoupled from the proximal coupling feature of the intracorporeal device and while a distal end of the at least one of the sheath or delivery catheter remains proximate to the deployment site.

2. The intracorporeal device delivery system of claim 1, further comprising a hub coupled to a proximal end of the delivery catheter.

3. The intracorporeal device delivery system of claim 1, wherein the delivery catheter includes the lumen, the lumen having a cross-sectional area sufficient and configured to be utilized as the conduit from which the calibration pressure measurements are obtained.

4. The intracorporeal device delivery system of claim 1, wherein the sheath includes the lumen, the lumen having a cross-sectional area greater than a cross-sectional area of the delivery catheter such that an annular volume is defined between the delivery catheter and a wall of the delivery catheter lumen, the annular volume sufficient and configured to be utilized as the conduit from which pressure measurements are obtained at the deployment site after the distal coupling feature of the delivery catheter is decoupled from the proximal coupling feature of the intracorporeal device and while a distal end of the sheath remains proximate to the deployment site.

5. The intracorporeal device delivery system of claim 1, wherein the lumen further comprises first and second lumen, the first lumen provided in the sheath and configured to receive the delivery catheter, the second lumen provided in the delivery catheter.

6. The intracorporeal device delivery system of claim 1, further comprising a hub at a proximal end of the lumen, the hub and proximal end of the lumen configured to communicate with a gauge to obtain the pressure measurements, through the lumen, at the deployment site.

7. The intracorporeal device delivery system of claim 6, wherein the hub comprises a shaft manipulation feature coupled to the delivery catheter, the shaft manipulation feature configured to release the distal coupling feature from the proximal coupling feature.

8. The intracorporeal device delivery system of claim 7, wherein the shaft manipulation feature is a rotatable knob coupled to the delivery shaft such that rotation of the rotatable knob rotates the delivery shaft to decouple the distal coupling feature from the proximal coupling feature.

9. The intracorporeal device delivery system of claim 6, wherein the hub comprises at least one port in communication with an auxiliary lumen such that the port is in fluid communication with a distal end of the auxiliary lumen.

10. The intracorporeal device delivery system of claim 9, wherein the auxiliary lumen is a delivery shaft lumen in the sheath.

11. The intracorporeal device delivery system of claim 1, wherein the distal coupling feature comprises a tether wire having a distal portion configured to secure the intracorporeal device to the delivery catheter.

12. The intracorporeal device delivery system of claim 11, wherein the proximal coupling feature comprises a flexible wire loop coupled to the device body, the tether wire configured to couple the wire loop to the delivery catheter.

13. A method for delivering an intracorporeal device, comprising:
advancing a sheath along vasculature to a deployment site;
providing the intracorporeal device comprising a proximal coupling feature and a device body, wherein the intracorporeal device is a pressure sensor;
coupling a distal coupling feature of a delivery catheter to the proximal coupling feature of the intracorporeal device;
at least one of the sheath or delivery catheter including a lumen having a proximal end and a distal end,
translating the delivery catheter within the sheath such that the intracorporeal device and the distal end of the lumen are proximate to the deployment site;
decoupling the distal coupling feature of the delivery catheter from the proximal coupling feature of the intracorporeal device;
after the decoupling, and while a distal end of the at least one of the sheath or delivery catheter remains proximate to the deployment site, utilizing the lumen as a conduit to obtain pressure measurements; and utilize the pressure measurements to calibrate the intracorporeal device.

14. The method of claim 13, further comprising providing a hub coupled to a proximal end of at least one of the sheath or the delivery catheter.

15. The method of claim 13, wherein the delivery catheter includes the lumen, the lumen having a cross-sectional area sufficient and configured to be utilized as the conduit from which the calibration pressure measurements are obtained.

16. The method of claim 13, further comprising providing the lumen in the sheath with a cross-sectional area greater than a cross-sectional area of the delivery catheter such that an annular volume is defined between the delivery catheter and a wall of the delivery catheter lumen, the annular volume sufficient to be utilized as the conduit from which pressure measurements are obtained at the deployment site after the distal coupling feature of the delivery catheter is decoupled from the proximal coupling feature of the intracorporeal device and while a distal end of the sheath remains proximate to the deployment site.

17. The method of claim 13, further comprising providing a first lumen in the sheath to receive the delivery catheter and providing a second lumen in the delivery catheter.

18. The method of claim 13, further comprising providing a hub at a proximal end of the lumen; coupling a gauge in communication with the hub and proximal end of the lumen; and utilizing the gauge to obtain the pressure measurements, through the lumen, at the deployment site.

19. The method of claim 18, wherein the hub comprises a shaft manipulation feature coupled to the delivery catheter, the method further comprising utilizing the shaft manipulation feature to release the distal coupling feature from the proximal coupling feature.

20. The method of claim 19, wherein the shaft manipulation feature is a rotatable knob coupled to the delivery shaft such that rotation of the rotatable knob rotates the delivery shaft to decouple the distal coupling feature from the proximal coupling feature.

21. The method of claim 18, wherein the hub comprises at least one port in communication with an auxiliary lumen such that the port is in fluid communication with a distal end of the auxiliary lumen.

22. The method of claim 21, wherein the auxiliary lumen is a delivery shaft lumen in the sheath.

23. The method of claim 13, wherein the distal coupling feature comprises a tether wire having a distal portion, the method further comprising utilizing the distal portion of the tether wire to couple the intracorporeal device to the delivery catheter.

24. The method of claim 23, wherein the proximal coupling feature comprises a flexible wire loop coupled to the device body, the method further comprising coupling the distal portion of the tether wire with the wire loop.

* * * * *